United States Patent
Silverman et al.

(10) Patent No.: US 12,083,113 B2
(45) Date of Patent: *Sep. 10, 2024

(54) USE OF NEURONAL NITRIC OXIDE SYNTHASE INHIBITORS FOR IMMUNOTHERAPY IN MELANOMA PATIENTS

(71) Applicants: Northwestern University, Evanston, IL (US); Chapman University, Orange, CA (US)

(72) Inventors: Richard B. Silverman, Winnetka, IL (US); Sun Yang, Lake Forest, CA (US)

(73) Assignees: Northwestern University, Evanston, IL (US); Chapman University, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/942,928

(22) Filed: Sep. 12, 2022

(65) Prior Publication Data

US 2023/0017126 A1    Jan. 19, 2023

Related U.S. Application Data

(63) Continuation of application No. 16/703,009, filed on Dec. 4, 2019, now Pat. No. 11,439,632.

(60) Provisional application No. 62/775,534, filed on Dec. 5, 2018.

(51) Int. Cl.
| | |
|---|---|
| A61K 31/47 | (2006.01) |
| A61K 31/381 | (2006.01) |
| A61K 31/4164 | (2006.01) |
| A61K 31/495 | (2006.01) |
| A61K 38/21 | (2006.01) |
| A61P 35/00 | (2006.01) |
| C07K 16/28 | (2006.01) |

(52) U.S. Cl.
CPC ............ *A61K 31/47* (2013.01); *A61K 31/381* (2013.01); *A61P 35/00* (2018.01); *A61K 31/4164* (2013.01); *A61K 31/495* (2013.01); *A61K 38/212* (2013.01); *C07K 16/2818* (2013.01)

(58) Field of Classification Search
CPC .. A61K 31/47; A61K 31/381; A61K 31/4164; A61K 31/495; A61K 38/212; A61P 35/00; C07K 16/2818
See application file for complete search history.

(56) References Cited

U.S. PATENT DOCUMENTS

| | | |
|---|---|---|
| 6,274,557 B1 | 8/2001 | Silverman |
| 6,803,486 B2 | 10/2004 | Silverman |
| 7,470,790 B2 | 12/2008 | Silverman |
| 7,470,815 B1 | 12/2008 | Silverman |
| 7,994,326 B2 | 8/2011 | Silverman |
| 8,158,658 B2 | 4/2012 | Silverman |
| 8,278,084 B2 | 10/2012 | Silverman |
| 8,299,100 B2 | 10/2012 | Silverman |
| 8,389,731 B2 | 3/2013 | Silverman |
| 8,557,552 B2 | 10/2013 | Silverman |
| 8,618,143 B1 | 12/2013 | Silverman |
| 8,642,282 B2 | 2/2014 | Meyskens |
| 8,697,879 B2 | 4/2014 | Silverman |
| 8,735,606 B2 | 5/2014 | Silverman |
| 8,829,187 B1 | 9/2014 | Silverman |
| 8,927,730 B2 | 1/2015 | Silverman |
| 8,932,842 B2 | 1/2015 | Silverman |
| 9,090,589 B2 | 7/2015 | Silverman |
| 9,120,750 B2 | 9/2015 | Silverman |
| 9,212,144 B2 | 12/2015 | Silverman |
| 9,212,161 B2 | 12/2015 | Silverman |
| 9,242,957 B2 | 1/2016 | Silverman |
| 9,416,106 B2 | 8/2016 | Silverman |
| 9,663,468 B2 | 5/2017 | Silverman |
| 9,682,950 B2 | 6/2017 | Silverman |
| 9,701,661 B2 | 7/2017 | Silverman |
| 9,732,037 B2 | 8/2017 | Silverman |
| 9,758,507 B2 | 9/2017 | Silverman |
| 9,765,055 B2 | 9/2017 | Silverman |
| 9,783,500 B2 | 10/2017 | Silverman |
| 9,878,996 B2 | 1/2018 | Silverman |
| 9,951,014 B2 | 4/2018 | Silverman |
| 10,167,260 B2 | 1/2019 | Silverman |
| 11,439,632 B2 * | 9/2022 | Silverman .............. A61K 31/47 |
| 2003/0119751 A1 | 6/2003 | Silverman |
| 2005/0107369 A1 | 5/2005 | Silverman |
| 2005/0159363 A1 | 7/2005 | Silverman |
| 2008/0108814 A1 | 5/2008 | Silverman |
| 2008/0176907 A1 | 7/2008 | Silverman |
| 2008/0234237 A1 | 9/2008 | Maddaford |

(Continued)

OTHER PUBLICATIONS

Jiang, G., et al. "Dacarbazine combined targeted therapy versus dacarbazine alone in patients with malignant melanoma: a meta-analysis." PLoS One 9.12 (2014): e111920.
Mojic, M. et al. "The dark side of IFN-?: its role in promoting cancer immunoevasion." International journal of molecular sciences 19.1 (2018): 89.
Quirt, I., et al. Temozolomide for the treatment of metastatic melanoma. Current Oncology, 2007, 14(1), 27.
Sunshine, J. et al. "Pd-1/pd-I1 inhibitors." Current opinion in pharmacology 23 (2015): 32-38.
Tarhini, A.A. "IFN-a in the treatment of melanoma." The Journal of Immunology 189.8 (2012): 3789-3793.
International Searching Authority. International Search Report and Written Opinion for application PCT/US2019/064398. Mailed on Mar. 19, 2020.

(Continued)

*Primary Examiner* — Daniel R Carcanague
(74) *Attorney, Agent, or Firm* — Quarles & Brady LLP

(57) ABSTRACT

Disclosed herein are methods and compositions for administering immunotherapy to a subject in need thereof and for treating a subject in need thereof, where in the methods the subject is administered an effective amount of an inhibitor of nNOS for inducing an immunotherapeutic response in the subject and for treating the subject. The disclosed methods and composition may be utilized for treating a subject having a cell proliferative disease or disorder such as melanoma.

24 Claims, 17 Drawing Sheets

(56) References Cited

U.S. PATENT DOCUMENTS

| | | |
|---|---|---|
| 2009/0104677 A1 | 4/2009 | Silverman |
| 2010/0009975 A1 | 1/2010 | Ramnauth |
| 2010/0190230 A1 | 7/2010 | Silverman |
| 2010/0203613 A1 | 8/2010 | Silverman |
| 2010/0292484 A1 | 11/2010 | Silverman |
| 2012/0004415 A1 | 1/2012 | Silverman |
| 2012/0088798 A1 | 4/2012 | Silverman |
| 2012/0122855 A1 | 5/2012 | Ramnauth |
| 2012/0238016 A1 | 9/2012 | Meyskens |
| 2012/0258513 A1 | 10/2012 | Silverman |
| 2013/0040359 A1 | 2/2013 | Silverman |
| 2014/0066635 A1 | 3/2014 | Silverman |
| 2014/0147920 A1 | 5/2014 | Silverman |
| 2014/0163016 A1 | 6/2014 | Ramnauth |
| 2014/0228578 A1 | 8/2014 | Silverman |
| 2014/0256016 A1 | 9/2014 | Silverman |
| 2014/0256958 A1 | 9/2014 | Silverman |
| 2015/0210644 A1 | 7/2015 | Silverman |
| 2015/0252020 A1 | 9/2015 | Silverman |
| 2015/0368201 A1 | 12/2015 | Silverman |
| 2016/0009690 A1 | 1/2016 | Silverman |
| 2016/0096806 A1 | 4/2016 | Silverman |
| 2016/0096821 A1 | 4/2016 | Silverman |
| 2016/0122302 A1 | 5/2016 | Silverman |
| 2016/0152590 A1 | 6/2016 | Silverman |
| 2016/0347713 A1 | 12/2016 | Silverman |
| 2016/0368877 A1 | 12/2016 | Silverman |
| 2017/0260165 A1 | 9/2017 | Silverman |
| 2017/0275278 A1 | 9/2017 | Silverman |
| 2017/0298021 A1 | 10/2017 | Silverman |
| 2020/0377481 A1 | 12/2020 | Silverman et al. |

OTHER PUBLICATIONS

Do; J. Med. Chem. 2019, 62, 2690-2707. http://dx.doi.org/10.1021/acs.jmedchem.8b02032 (Year: 2019).

Do; J. Med. Chem. 2017, 60, 22, 9360-9375. https://doi.org/10.1021/acs.jmedchem.7b01356 (Year: 2017).

Yarlagadda; BBA—Reviews on Cancer 2017, 1868, 500-509. https://doi.org/10.1016/j.bbcan.2017.09.005 (Year: 2017).

Li; Biochemistry 2018, 57, 6319-6325. DOI: 10.1021/acs.biochem.8b00895 (Year: 2018).

Ahmed B, et al. Expression of the neuronal isoform of nitric oxide synthase (nNOS) and its inhibitor, protein inhibitor of nNOS, in pigment cell lesions of the skin. Br J Dermatol 141: 12-9, 1999.

Albina JE, et al. Nitric-Oxide Production Is Required for Murine Resident Peritoneal-Macrophages to Suppress Mitogen-Stimulated T-Cell Proliferation—Role of Ifn-Gamma in the Induction of the Nitric Oxide-Synthesizing Pathway. Journal of Immunology 147: 144-148, 1991.

Audrito V, et al. PD-L1 up-regulation in melanoma increases disease aggressiveness and is mediated through miR-17-5p. Oncotarget 8: 15894-15911, 2017.

Bald T, et al. Immune cell-poor melanomas benefit from PD-1 blockade after targeted type I IFN activation. Cancer Discov 4: 674-87, 2014.

Bhat P, et al. Interferon-gamma derived from cytotoxic lymphocytes directly enhances their motility and cytotoxicity. Cell Death Dis 8: e2836, 2017.

Buettner R, et al. Activated STAT signaling in human tumors provides novel molecular targets for therapeutic Intervention. Clin Cancer Res 8: 945-54, 2002.

Byrne EH, et al. Immune and molecular correlates in melanoma treated with immune checkpoint blockade. Cancer 123: 2143-2153, 2017.

Cinelli MA, et al. Nitrile in the Hole: Discovery of a Small Auxiliary Pocket in Neuronal Nitric Oxide Synthase Leading to the Development of Potent and Selective 2-Aminoquinoline Inhibitors. J Med Chem 60: 3958-3978, 2017.

Cinelli MA, et al. Phenyl Ether- and Aniline-Containing 2-Aminoquinolines as Potent and Selective Inhibitors of Neuronal Nitric Oxide Synthase. J Med Chem 58: 8694-712, 2015.

Concha-Benavente F, et al. Identification of the Cell-Intrinsic and -Extrinsic Pathways Downstream of EGFR and IFNgamma That Induce PD-L1 Expression in Head and Neck Cancer. Cancer Res 76: 1031-43, 2016.

Ferrantini M, et al. IFN-alpha 1 gene expression into a metastatic murine adenocarcinoma (TS/A) results in CD8+ T cell-mediated tumor rejection and development of antitumor immunity. Comparative studies with IFN-gamma-producing TS/A cells. J Immunol 153: 4604-15, 1994.

Ferrer P, et al. Nitric oxide mediates natural polyphenol-induced Bcl-2 down-regulation and activation of cell death in metastatic B16 melanoma. J Biol Chem 282: 2880-90, 2007.

Garcia-Diaz A, et al. Interferon Receptor Signaling Pathways Regulating PD-L1 and PD-L2 Expression. Cell Rep 19: 1189-1201, 2017.

Gowrishankar K, et al. Inducible but not constitutive expression of PD-L1 in human melanoma cells is dependent on activation of NF-kappaB. PLoS One 10: e0123410, 2015.

Halliday GM, et al. The suppression of immunity by ultraviolet radiation: UVA, nitric oxide and DNA damage. Photochem Photobiol Sci 3: 736-40, 2004.

Huang, H., et al. "Potent and selective double-headed thiophene-2-carboximidamide inhibitors of neuronal nitric oxide synthase for the treatment of melanoma." Journal of medicinal chemistry 57.3 (2014): 686-700.

Jaiswal M, et al. Inflammatory cytokines induce DNA damage and inhibit DNA repair in cholangiocarcinoma cells by a nitric oxide-dependent mechanism. Cancer Res 60: 184-90, 2000.

Joshi M, et al. Nitric oxide synthase activity is up-regulated in melanoma cell lines: a potential mechanism for metastases formation. Melanoma Res 6: 121-6, 1996.

Juneja VR, et al. PD-L1 on tumor cells is sufficient for immune evasion in immunogenic tumors and inhibits CD8 T cell cytotoxicity. J Exp Med, 2017.

Kaunitz GJ, et al. Melanoma subtypes demonstrate distinct PD-L1 expression profiles. Lab Invest 97: 1063-1071, 2017.

Kortylewski M, et al. Targeting STAT3 affects melanoma on multiple fronts. Cancer Metastasis Rev 24: 315-27, 2005.

Lee IC, et al. Serum interferon gamma level predicts recurrence in hepatocellular carcinoma patients after curative treatments. Int J Cancer 133: 2895-902, 2013.

Liu Q, et al. Melanoma NOS1 expression promotes dysfunctional IFN signaling. J Clin Invest 124: 2147-59, 2014.

Lollini PL, et al. Enhancement of experimental metastatic ability by tumor necrosis factor-alpha alone or in combination with interferon-gamma. Clin Exp Metastasis 8: 215-24, 1990.

Lollini PL, et al. Re:Randomized trial of adjuvant human interferon gamma versus observation in high-risk cutaneous melanoma: a Southwest Oncology Group study. J Natl Cancer Inst 88: 926-7, 1996.

Lorenz P, et al. Oxyresveratrol and resveratrol are potent antioxidants and free radical scavengers: effect on nitrosative and oxidative stress derived from microglial cells. Nitric Oxide 9: 64-76, 2003.

Macmicking J, et al. Nitric oxide and macrophage function. Annu Rev Immunol 15: 323-50, 1997.

Mauldin IS, et al. Intratumoral interferon-gamma increases chemokine production but fails to increase T cell infiltration of human melanoma metastases. Cancer Immunol Immunother 65: 1189-99, 2016.

Meissl K, et al. The good and the bad faces of STAT1 in solid tumours. Cytokine 89: 12-20, 2017.

Mimura K, et al. PD-L1 expression is mainly regulated by interferon gamma associated with JAK-STAT pathway in gastric cancer. Cancer Sci 109: 43-53, 2018.

Pensa AV, et al. Hydrophilic, Potent, and Selective 7-Substituted 2-Aminoquinolines as Improved Human Neuronal Nitric Oxide Synthase Inhibitors. J Med Chem 60: 7146-7165, 2017.

Prasad R, et al. Crosstalk Among UV-Induced Inflammatory Mediators, DNA Damage and Epigenetic Regulators Facilitates Suppression of the Immune System. Photochem Photobiol, 2016.

Ray S, et al. Regulation of signal transducer and activator of transcription 3 enhanceosome formation by apurinic/apyrimidinic endonuclease 1 in hepatic acute phase response. Mol Endocrinol 24: 391-401, 2010.

(56) References Cited

OTHER PUBLICATIONS

Schultz J, et al. Tumor-promoting role of signal transducer and activator of transcription (Stat)1 in late-stage melanoma growth. Clin Exp Metastasis 27: 133-40, 2010.

Simon S, et al. PD-1 expression on tumor-specific T cells: Friend or foe for immunotherapy? Oncoimmunology 7: e1364828, 2017.

Simons DL, et al. Interferon signaling patterns in peripheral blood lymphocytes may predict clinical outcome after high-dose interferon therapy in melanoma patients. J Transl Med 9: 52, 2011.

Tanese K, et al. Cell Surface CD74-MIF Interactions Drive Melanoma Survival in Response to Interferon-gamma. J Invest Dermatol 135: 2775-84, 2015.

Tang CH, et al. Depletion of endogenous nitric oxide enhances cisplatin-induced apoptosis in a p53-dependent manner in melanoma cell lines. J Biol Chem 279: 288-98, 2004.

Vannini F, et al. The dual role of iNOS in cancer. Redox Biol 6: 334-43, 2015.

Weinmann H. Cancer Immunotherapy: Selected Targets and Small-Molecule Modulators. ChemMedChem 11: 450-66, 2016.

Yamazaki T, et al. Blockade of B7-H1 on macrophages suppresses CD4+ T cell proliferation by augmenting IFN-gamma-induced nitric oxide production. J Immunol 175: 1586-92, 2005.

Yang S, et al. Alterations in activating protein 1 composition correlate with phenotypic differentiation changes induced by resveratrol in human melanoma. Mol Pharmacol 67: 298-308, 2005.

Yang S, et al. Alterations in the expression of the apurinic/apyrimidinic endonuclease-1/redox factor-1 (APE/Ref-1) in human melanoma and identification of the therapeutic potential of resveratrol as an APE/Ref-1 inhibitor. Mol Cancer Ther 4: 1923-35, 2005.

Yang S, et al. Apurinic/apyrimidinic endonuclease/redox effector factor-1(APE/Ref-1): a unique target for the prevention and treatment of human melanoma. Antioxid Redox Signal 11: 639-50, 2009.

Yang Z, et al. Nitric oxide initiates progression of human melanoma via a feedback loop mediated by apurinic/apyrimidinic endonuclease-1/redox factor-1, which is inhibited by resveratrol. Mol Cancer Ther 7: 3751-60, 2008.

Yang Z, et al. Targeting nitric oxide signaling with nNOS inhibitors as a novel strategy for the therapy and prevention of human melanoma. Antioxid Redox Signal 19: 433-47, 2013.

Yue EW, et al. INCB24360 (Epacadostat), a Highly Potent and Selective Indoleamine-2,3-dioxygenase 1 (IDO1) Inhibitor for Immuno-oncology. ACS Med Chem Lett 8: 486-491, 2017.

Zaidi MR, et al. Interferon-gamma links ultraviolet radiation to melanomagenesis in mice. Nature 469: 548-53, 2011.

Paretsky JM, et al. Mutations Associated with Acquired Resistance to PD-1 Blockade in Melanoma. N Engl J Med 375: 819-29, 2016.

Tong; Scientific Reports 2022, 12, 1701. DOI: 10.1038/s41598-022-05394-6 (Year: 2022).

Quirt I et al.: "Temozolomide for the treatment of metastatic melanoma: a systematic review"; Oncologist, vol. 12, No. 9, pp. 1114-1123, DOI: 10.1634/theoncologist. 12-9-1114, Sep. 1, 2007 (Sep. 1, 2007).

* cited by examiner

USE OF NEURONAL NITRIC OXIDE SYNTHASE INHIBITORS FOR IMMUNOTHERAPY IN MELANOMA PATIENTS

CROSS-REFERENCE TO RELATED APPLICATIONS

The present application is continuation of U.S. application Ser. No. 16/703,009, filed Dec. 4, 2019, which claims the benefit of priority under 35 U.S.C. 119(e) to U.S. Provisional Application No. 62/775,534, filed on Dec. 5, 2018, the contents of which are incorporated herein by reference in their entireties.

STATEMENT REGARDING FEDERALLY SPONSORED RESEARCH OR DEVELOPMENT

This invention was made with government support under GM049725 awarded by the National Institutes of Health. The government has certain rights in the invention.

BACKGROUND

The field of the invention relates to methods for administering immunotherapy to a subject in need thereof. In particular, the field of the invention relates to the use of neuronal nitric oxide synthase (nNOS) inhibitors in methods for administering immunotherapy to subjects having cell proliferative diseases and disorders such as cancer, in particular melanoma.

Human cutaneous melanoma (CM) incidence rates continue to increase in recent decades, making this disease a rising public health concern. Melanoma accounts for less than 1% of all skin cancer cases, but the vast majority of skin cancer deaths. With a high rate of genomic mutations. (43), it is the deadliest and most aggressive form of skin cancer with a five-year survival rate of 15-20% for patients with distant metastasis (1). (See, e.g., Lawrence et al., "Mutational heterogeneity in cancer and the search for new cancer-associated genes," Nature 499: 214-218, 2013; and 2017. Key Statistics for Melanoma Skin Cancer American Cancer Society. https://www.cancer.org/cancer/melanoma-skin-cancer/about/key-statistics.html 2017 Apr. 17; the contents of which are incorporated herein by reference in their entireties). Early identification coupled with surgical excision has the best outcome for patients. (See, e.g., Rutkowski, et al., "Surgery of Primary Melanomas," Cancers. 2010 June; 2(2): 824-841; and Voss et al., "Improving outcomes in patients with melanoma strategies to ensure an early diagnosis," Patient Relat Outcome Meas. 2015; 6: 229-242; the contents of which are incorporated herein by reference in their entireties). Because of the diverse resistance mechanisms exploited by the disease, the efficiency of traditional cytotoxic chemotherapy is very limited, which is also associated with severe toxicities due to a lack of specificity in their mechanism of action.

Interferon-gamma (IFN-γ), which is produced by human immune cells, has been shown to play a role in melanoma development and progression. The present inventors have found that IFN-γ induces expression of neuronal nitric oxide synthase (nNOS). Further, the inventors have found that by inhibiting nNOS, the expression of signal transducer and activator of transcription 1 and 3 (STAT 1/3), which is upregulated by IFN-γ, and the expression of PD-L1 are inhibited. PD-L1 increases melanoma progression associated with immunosuppression.

The inventors have demonstrated, for the first time, the role of neuronal nitric oxide synthase in IFN-γ-stimulated melanoma progression both in vitro and in vivo, which strongly implicates the use of nNOS-selective inhibitors as an innovative first-in-class approach for the treatment of melanoma. The inventors' research also demonstrates the important novel role of nNOS in regulating IFN-γ-induced PD-L1 expression, which identifies nNOS as a new target for the development of an effective immunotherapy for melanoma patients using nNOS-selective inhibitors. As such, the inventors have found that by inhibiting nNOS, melanoma growth can be effectively inhibited.

The inventors' findings have implications for treating melanoma. However, the inventors' findings also may having implications for treating any cell proliferative disease or disorder whose growth or progression is stimulated by increased expression of nNOS, In particular, the inventors' findings have implication for treating cell proliferative diseases and disorders whose growth or progression are stimulated by IFN-γ-induced expression of nNOS and subsequent expression of immunomodulatory proteins in the subject such as PD-L1.

SUMMARY

Disclosed herein are methods and compositions for administering immunotherapy to a subject in need thereof and for treating a subject in need thereof, where in the methods the subject is administered an effective amount of an inhibitor of nNOS for inducing an immunotherapeutic response in the subject and for treating the subject. The disclosed methods and composition may be utilized for treating a subject having a cell proliferative disease or disorder such as melanoma.

The disclosed methods and compositions may be utilized for treating a subject having a cell proliferative disease or disorder whose growth or progression is stimulated by IFN-γ such as melanoma. The methods typically comprise administering to the subject an effective amount of an inhibitor of nNOS for decreasing expression of an immunomodulatory protein in the subject, such as an effective amount of an inhibitor of nNOS for decreasing expression of PD-L1 in the subject.

In the disclosed methods, the subject is administered an inhibitor of nNOS. In the disclosed methods, the subject also may be administered additional therapeutic agents such as an inhibitor of PD-L1 or an inhibitor of PD-1.

DETAILED DESCRIPTION

Figure 1:
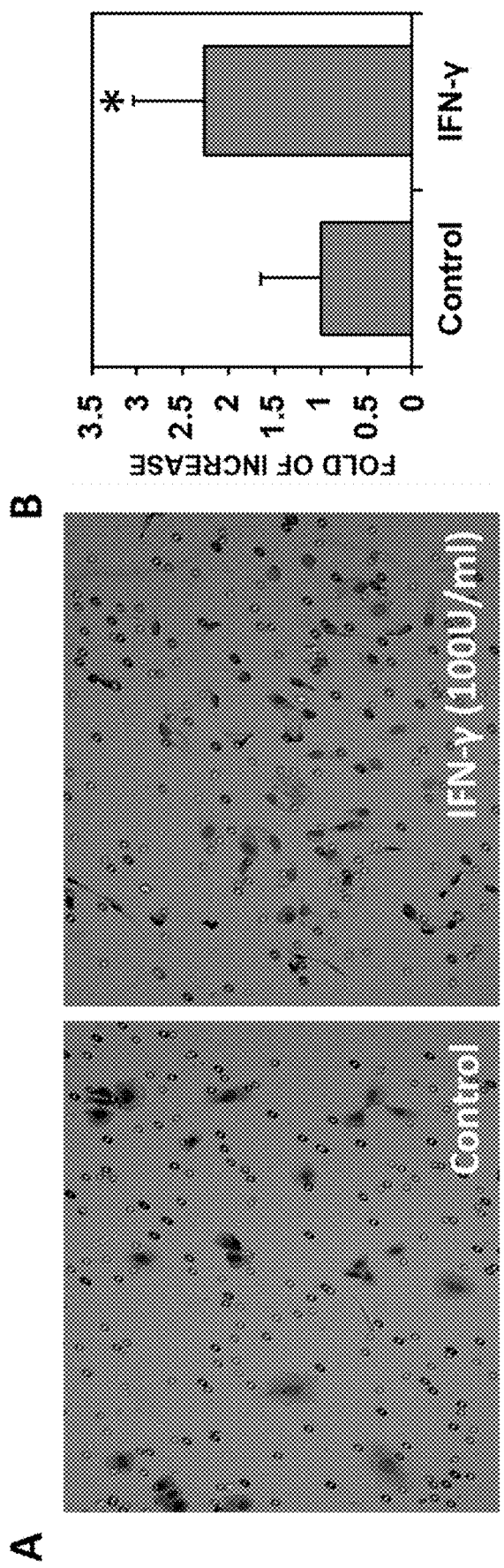
FIG. 1. A) Effect of IFN-γ on melanoma invasion potential detected by matrigel invasion assay. The represented data were from A375 metastatic melanoma cells treated with IFN-γ. *, p<0.05 compared to control. B) Adhesion analysis. A375 melanoma cells were seeded on top of fibroblast monolayer and incubated with IFN-γ for 1 hour, followed by MTT assay. *, p<0.05 compared to control.

The present invention is described herein using several definitions, as set forth below and throughout the application.

Definitions

Unless otherwise specified or indicated by context, the terms "a", "an", and "the" mean "one or more." For example, "a compound" or "an inhibitor" should be interpreted to mean "one or more compounds" and "one or more inhibitors," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

The disclosed methods relate to methods of treating a subject in need thereof. In particular, the disclosed methods related to methods of administering immunotherapy to a subject in need thereof.

As used herein, a "subject" may be interchangeable with "patient" or "individual" and means an animal, which may be a human or non-human animal, in need of treatment, for example, treatment that includes administering an inhibitor of neuronal nitric oxide synthase (i.e., an nNOS inhibitor).

A "subject in need of treatment" may include a subject having a cell proliferative disease, disorder, or condition such as cancer. Cancers may include, but are not limited to adenocarcinoma, leukemia, lymphoma, melanoma, myeloma, sarcoma, and teratocarcinoma and particularly cancers of the adrenal gland, bladder, blood, bone, bone marrow, brain, breast, cervix, gall bladder, ganglia, gastrointestinal tract, heart, kidney, liver, lung, muscle, ovary, pancreas, parathyroid, prostate, skin, testis, thymus, and uterus.

A "subject in need of treatment" in particular may include a subject having or at risk for developing melanoma. More particularly, a "subject in need of treatment" may include a subject having or at risk for developing Stage I melanoma, Stage II melanoma, Stage III melanoma, or Stage IV melanoma.

A "subject in need of treatment" in particular may include a subject having melanoma and exhibiting or at risk for developing IFN-γ-stimulated melanoma progression. A "subject in need of treatment" in particular may include a subject having melanoma and exhibiting or at risk for developing melanoma characterized by elevated expression levels of nNOS (optionally where the elevated expression levels of nNOS are induced by IFN-γ). A "subject in need of treatment" in particular may include a subject having melanoma and exhibiting or at risk for developing melanoma characterized by elevated expression levels of signal transducer and activator of transcription 1 and 3 (STAT 1/3) (optionally where the elevated expression levels of STAT 1/3 are induced by IFN-γ). A "subject in need of treatment" in particular may include a subject having melanoma and exhibiting or at risk for developing melanoma characterized by elevated expression levels of programmed death-ligand 1 (PD-L1) (optionally where the elevated expression levels of PD-L1 are induced by IFN-γ).

Use of Neuronal Nitric Oxide Synthase Inhibitors for Immunotherapy in Cancer Patients The disclosed subject matter related to method for administering immunotherapy to a subject in need thereof. The methods typically include administering to the subject an effective amount of an inhibitor of neuronal nitric oxide synthase (nNOS) for inducing an immunotherapeutic response.

In some embodiments of the disclosed methods, the subject may have a cell proliferative disease or disorder or may be at risk for developing a cell proliferative disease or disorder as disclosed herein and as known in the art. In particular, the subject may have melanoma or may be at risk for developing melanoma (e.g., Stage I melanoma, Stage II melanoma, Stage III melanoma, or Stage IV melanoma).

In some embodiments of the disclosed methods, the subject may have melanoma and is exhibiting or may be at risk for developing IFN-γ-stimulated melanoma progression. In further embodiments of the disclosed methods, the subject may have melanoma and is exhibiting or is at risk for developing melanoma characterized by elevated expression levels of nNOS (e.g., elevated expression levels of nNOS that are induced by IFN-γ). In further embodiments of the disclosed methods, the subject may have melanoma and is exhibiting or is at risk for developing melanoma characterized by elevated expression levels of signal transducer and activator of transcription 1 and 3 (STAT 1/3) (e.g., elevated expression levels of STAT 1/3 that are induced by IFN-γ). In even further embodiments of the disclosed methods, the subject may have melanoma and is exhibiting or is at risk for developing melanoma characterized by elevated expression levels of programmed death-ligand 1 (PD-L1) (e.g., elevated expression levels of PD-L1 that are induced by IFN-γ).

In the disclosed methods, the subject of the methods typically is administered an inhibitor of neuronal nitric oxide synthase (nNOS). Inhibitors of nNOS, pharmaceutical compositions comprising inhibitors of nNOS, and methods of administering inhibitors of nNOS as therapy are disclosed herein and are known in the art. (See, e.g., U.S. Published Application Nos.: 20170298021, "2-Aminopyridine-based Selective Neuronal Nitric Oxide Synthase Inhibitors"; 20170275278, "Mammalian and Bacterial Nitric Oxide Synthase Inhibitors"; 20170260165, "2-Imidazolyl-Pyrimidine Scaffolds as Potent and Selective Inhibitors of Neuronal Nitric Oxide Synthase"; 20160368877, "2-Aminoquinoline-Based Compounds for Potent and Selective Neuronal Nitric Oxide Synthase Inhibition"; 20160347713, "2-Aminopyridine-based Selective Neuronal Nitric Oxide Synthase Inhibitors"; 20160152590, "Thiophene-2-carboximidamide Based Selective Neuronal Nitric Oxide Synthase Inhibitors"; 20160122302, "Mammalian and Bacterial Nitric Oxide Synthase Inhibitors"; 20160096821, "Chiral Synthesis of Pyrrolidine Core Compounds en route to Neuronal Nitric Oxide Synthase Inhibitors"; 20160096806, "2-Aminoquinoline-Based Compounds for Potent and Selective Neuronal Nitric Oxide Synthase Inhibition"; 20160009690, "2-Imidazolyl-Pyrimidine Scaffolds as Potent and Selective Inhibitors of Neuronal Nitric Oxide Synthase"; 20150368201, "2-Aminopyridine-based Selective Neuronal Nitric Oxide Synthase Inhibitors"; 20150252020, "Intramolecular Hydrogen-Bonded Nitric Oxide Synthase Inhibitors"; 20150210644, "2-Aminoquinoline-based Compounds for Potent and Selective Neuronal Nitric Oxide Synthase Inhibition"; 20140256958, "Thiophene-2-carboximidamide Based Selective Neuronal Nitric Oxide Inhibitors"; 20140256016, "2-Aminopyridine-based Selective Neuronal Nitric Oxide Synthase Inhibitors"; 20140228578, "Chiral Synthesis of Pyrrolidine Core Compounds en route to Neuronal Nitric Oxide Synthase Inhibitors"; 20140163016, "Benzoxazines, Benzothiazines, and Related Compounds having NOS Inhibitory Activity"; 20140147920, "Specific nNOS Inhibitors for the Therapy and Prevention of Human Melanoma"; 20140066635, "Thiophene-2-carboximidamide Based Selective Neuronal Nitric Oxide Inhibitors"; 20130040359, "Aminopyridine dimer compounds, compositions and related methods for neuronal nitric oxide synthase inhibition"; 20120258513, "Selective Neuronal Nitric Oxide Synthase Inhibitors"; 20120238016, "Specific nNOS Inhibitors for the Therapy And Prevention Of Human Melanoma"; 20120122855, "Benzoxazines, Benzothiazines, and Related Compounds having NOS Inhibitory Activity"; 20120088798, "Intramolecular Hydrogen-Bonded Nitric Oxide Synthase Inhibitors"; 20120004415, "Chiral Synthesis of Pyrrolidine Core Compounds en route to Neuronal Nitric Oxide Synthase Inhibitors"; 20100292484, "Chiral Pyrrolidine Core Compounds en route to Inhibitors of Nitric Oxide Synthase"; 20100203613, "Aminopyridine Dimer Compounds, Compositions and Related Methods for Neuronal Nitric Oxide Synthase Inhibition"; 20100190230, "Potent and Selective Neuronal Nitric Oxide Synthase Inhibitors with Improved Membrane Permeability"; 20100009975, "Benzoxazines, Benzothiazines, and Related Compounds having NOS Inhibitory Activity"; 20090104677, "Heteroaromatic Selective Inhibitors of Neuronal Nitric Oxide Synthase"; 20080234237, "Quinolone and Tetrahydroquinolone and Related Compound Having NOS Inhibitory Activity"; 20080176907, "NOS Inhibitors For Treatment Of Motor Deficit Disorders"; 20080108814, "Potent and highly selective heteroaromatic inhibitors of neuronal nitric oxide synthase"; 20050159363, "Selective neuronal nitric oxide synthase inhibitors"; 20050107369, "Heteroaromatic selective inhibitors of neuronal nitric oxide synthase"; and 20030119751, "Selective neuronal nitric oxide synthase inhibitors"; the contents of which are incorporated herein by reference in their entireties).

In some embodiments of the disclosed methods, the inhibitor of nNOS that is administered is the compound MAC-3-190 having a formula:

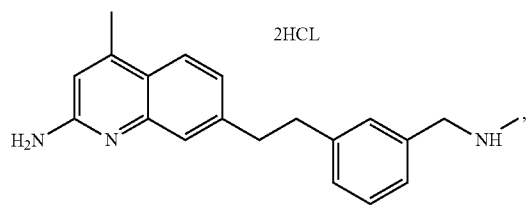

or suitable pharmaceutical salts, solvates, or hydrates thereof. The compound MAC-3-190 is disclosed as "compound 14" in U.S. Published Application No. 20160368877 (the content of which is incorporated herein by reference in its entirety).

The method of any of the foregoing claims, wherein the inhibitor of nNOS is the compound HH044 having a formula:

or suitable pharmaceutical salts, solvates, or hydrates thereof. The compound HH044 is disclosed as "compound 7" in U.S. Published Application No. 20160152590, (the content of which is incorporated herein by reference in its entirety).

In the disclosed methods, the subject typically is administered an inhibitor of NOS in order to induce an immunotherapeutic response. In some embodiments of the disclosed methods, the subject is administered an inhibitor of NOS which induces an immunotherapeutic response that includes inducing a decrease in expression of PD-L1. For example, in some embodiments of the disclosed methods where the subject has melanoma, the subject is administered an inhibitor of NOS which induces an immunotherapeutic response that includes a decrease in expression of PD-L1 in the melanoma.

In the disclosed methods, the subject typically is administered an inhibitor of NOS in order to induce an immunotherapeutic response. In some embodiments of the disclosed methods, the subject may be administered an additional therapeutic agent. For example, in some embodiments of the disclosed methods the subject is administered an inhibitor of NOS and further is administered a pharmaceutical composition that comprises IFN-α. Pharmaceutical compositions that comprise IFN-α are known in the art. (See, e.g., Roferon® A brand interferon alpha 2a, Intron® A/Erlif-eron®/Uniferon® brand interferon alpha 2b, and Multiferon® brand human leukocyte interferon-alpha (HuIFN-alpha-Le)).

In further embodiments of the disclosed methods, the subject is administered an inhibitor of NOS and further is administered a pharmaceutical composition that comprises a PD-L1 inhibitor and/or a PD-1 inhibitor. Pharmaceutical compositions that comprise a PD-L1 inhibitor are known in the art. (See, e.g., Atezolizumab (Tecentriq™) (Roche Genentech), Avelumab (Bavencio™) (Merck Serono), Durvalumab (Imfinzi™) (AstraZeneca), BMS-936559 (Bristol-Myers Squibb), and CK-301 (Checkpoint Therapeutics)). Pharmaceutical compositions that comprise a PD-1 inhibitor also are known in the art. (See, e.g., Pembrolizumab (Keytruda™) (Merck) and Nivolumab (Opdivo™) (Bristol-Myers Squibb).

In some embodiments of the disclosed methods the subject is administered an inhibitor of NOS and further is administered a pharmaceutical composition that comprises a chemotherapeutic agent for treating melanoma. In some embodiments of the disclosed methods, the subject is administered an inhibitor of NOS and further is administered dacarbazine. In other embodiments of the disclosed methods, the subject is administered an inhibitor of NOS and further is administered temozolomide to the subject.

ILLUSTRATIVE EMBODIMENTS

The following embodiments are illustrative and should not be interpreted to limit the scope of the claimed subject matter.

Embodiment 1. A method for administering immunotherapy to a subject in need thereof and/or a method for treating a subject in need thereof, the method comprising administering to the subject an effective amount of an inhibitor of neuronal nitric oxide synthase (nNOS) for inducing an immunotherapeutic response and/or an effective amount of an.

Embodiment 2. The method of embodiment 1, wherein the subject has a cell proliferative disease or disorder.

Embodiment 3. The method of embodiment 1 or embodiment 2, wherein the subject has melanoma.

Embodiment 4. The method of any of the foregoing embodiments, wherein the subject has or is at risk for developing Stage I melanoma, Stage II melanoma, Stage III melanoma, or Stage IV melanoma.

Embodiment 5. The method of any of the foregoing embodiments, wherein the subject has melanoma and is exhibiting or is at risk for developing IFN-γ-stimulated melanoma progression.

Embodiment 6. The method of any of the foregoing embodiments, wherein the subject has melanoma and is exhibiting or at risk for developing melanoma characterized by elevated expression levels of nNOS.

Embodiment 7. The method of any of the foregoing embodiments, wherein the subject has melanoma and is exhibiting or at risk for developing melanoma characterized by elevated expression levels of nNOS that are induced by IFN-γ.

Embodiment 8. The method of any of the foregoing embodiments, wherein the subject has melanoma and is exhibiting or at risk for developing melanoma characterized by elevated expression levels of signal transducer and activator of transcription 1 and 3 (STAT 1/3).

Embodiment 9. The method of any of the foregoing embodiments, wherein the subject has melanoma and is exhibiting or at risk for developing melanoma characterized by elevated expression levels of STAT 1/3 that are induced by IFN-γ.

Embodiment 10. The method of any of the foregoing embodiments, wherein the subject has melanoma and is exhibiting or at risk for developing melanoma characterized by elevated expression levels of programmed death-ligand 1 (PD-L1).

Embodiment 11. The method of any of the foregoing embodiments, wherein the subject has melanoma and is exhibiting or at risk for developing melanoma characterized by elevated expression levels of PD-L1 that are induced by IFN-γ.

Embodiment 12. The method of any of the foregoing embodiments, wherein the inhibitor of nNOS is the compound MAC-3-190 having a formula:

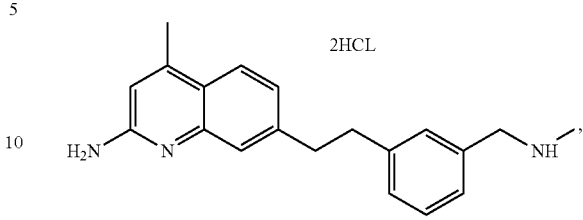

or suitable pharmaceutical salts, solvates, or hydrates thereof.

Embodiment 13. The method of any of the foregoing embodiments, wherein the inhibitor of nNOS is the compound HH044 having a formula:

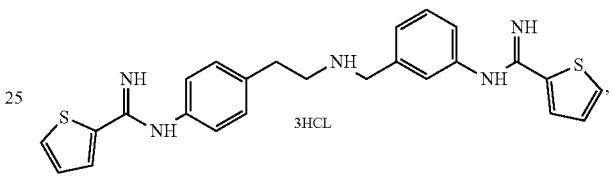

or suitable pharmaceutical salts, solvates, or hydrates thereof.

Embodiment 14. The method of any of the foregoing embodiments, wherein the immunotherapeutic response includes a decrease in expression of PD-L1.

Embodiment 15. The method of any of the foregoing embodiments, wherein the subject has melanoma and the immunotherapeutic response includes a decrease in expression of PD-L1 in the melanoma.

Embodiment 16. The method of any of the foregoing embodiments, further comprising administering to the subject IFN-α.

Embodiment 17. The method of any of the foregoing embodiments, further comprising administering to the subject a PD-L1 inhibitor (e.g., Atezolizumab) or a PD-1 inhibitor (e.g., Pembrolizumab or Nivolumab).

Embodiment 18. The method of any of the foregoing embodiments, further comprising administering chemotherapy to the subject.

Embodiment 19. The method of any of the foregoing embodiments, further comprising administering dacarbazine to the subject.

Embodiment 20. The method of any of the foregoing embodiments, further comprising administering temozolomide to the subject.

EXAMPLES

The following Examples are illustrative and are not intended to limit the scope of the claimed subject matter.
Title: The Role of Neuronal Nitric Oxide Synthase (nNOS) in Interferon-Gamma (IFN-γ)-Induced Melanoma Progression Reference is made to the manuscript Fong, S., Silverman, R., and Yang, S., "The Role of Neuronal Nitric Oxide Synthase (nNOS) in Interferon-Gamma (IFN-γ)-Induced Melanoma Progression," to be submitted for review and publication subsequent to the filing of the present application.

Abstract

Background: Interferon-gamma (IFN-γ), produced by human immune cells, has been shown to play a role in melanoma development and progression. However, the underlying mechanism is not completely understood.

Aim: We therefore investigated the role of neuronal nitric oxide synthase (nNOS)-mediated signal pathway in IFN-γ-stimulated melanoma progression both in vitro and in vivo, and determined whether such stimulation by IFN-γ is inhibited by blocking nNOS-nitric oxide (NO) signaling using pharmaceutical inhibitors.

Results: Our study shows that IFN-γ markedly induced the expression levels of nNOS in melanoma cells, while such induction was absent with treatment of IFN-alpha (IFN-α), a FDA-approved adjuvant therapy for melanoma. Consistently, intracellular NO levels also increased after IFN-γ exposure. STAT 1 and 3 were activated by IFN-γ treatment in melanoma cells, associated with increased level of phosphorylated-STAT1/3. Novel nNOS inhibitors effectively alleviate the IFN-γ-activated STAT1/3 at low concentration (304). Further reverse phase protein array (RPPA) analysis demonstrated that IFN-γ induced the expression of genes associated with melanoma proliferation, invasion, and immunosuppression, such as HIF1a, c-Myc, and programmed death-ligand 1 (PD-L1), while such changes were not observed after IFN-α exposure. Of note, PD-L1 expressions level were increased to 1.8-fold of control, while was absent with IFN-α treatment. The induction of PD-L1 by IFN-γ was also confirmed by flow cytometry and immunofluorescence staining. Blocking nNOS-mediated signal pathway using specific inhibitors was shown to effectively diminish IFN-γ-inducible PD-L1 in melanoma cells. In addition, using a xenograft melanoma model, our in vivo animal studies revealed that IFN-γ increased the tumor growth compared to control, which was reversed by the co-administration of nNOS inhibitor, MAC-3-190 (5 mg/kg/day). Another nNOS inhibitor, HH044, was shown to effectively inhibit tumor growth in vivo, associated with reduced PD-L1 expression levels in xenograft melanoma tumors.

Innovation: Our study, for the first time, demonstrated the important role of nNOS-mediated nitric oxide signal pathway in IFN-γ-stimulated melanoma progression.

Conclusion: Targeting nNOS using highly selective pharmaceutical inhibitors is a unique and effective strategy to improve the treatment of melanoma.

Introduction

Human cutaneous melanoma (CM) incidence rates continue to increase in recent decades, making this disease a rising public health concern. Melanoma accounts for less than 1% of all skin cancer cases, but the vast majority of skin cancer deaths. With a high rate of genomic mutation (43), it is the deadliest and most aggressive form of skin cancer with a five-year survival rate of 15-20% for patients with distant metastasis (1). Early identification coupled with surgical excision has the best outcome for patients. Due to the diverse resistance mechanisms exploited by the disease, the efficiency of traditional cytotoxic chemotherapy is very limited, which is also associated with severe toxicities due to lack of specificity in their mechanism of action.

It is well-documented that the tumor microenvironment (TME) can shelter cancer cells from immune response, thereby rendering them able to escape from effective immune surveillance. Immunotherapy has emerged as a promising new approach to melanoma treatment due to an increased understanding of the pathophysiology and role of the immune system in cancer. In recent years, there is considerable development in understanding the immunology of melanoma and translating it to robust therapeutic strategies. As a result, cancer therapy is currently undergoing a paradigm shift from classic cytotoxic agents toward identifying agents (mAb and small molecules) that afford restoration and/or activation of the immune system to break tumor-associated immune tolerance. Immunotherapy harnesses patients' own immune system by targeting specific biomarkers, which allows oncologists to tailor treatments based on the unique complexity of each patient's disease (21, 61). Despite the exciting developments, the revolutionary immunotherapy is mainly indicated for patients with unresectable or metastatic melanoma and disease progression on or after other treatments (27). In addition, the shortcomings of immune checkpoint inhibitors have also been identified due to a large population of melanoma patients failing to respond or quickly acquiring resistance to the therapy. Unfortunately, no biomarker has been identified to distinguish patients who would receive long-term benefits from immunotherapy. Furthermore, given the high incidence of severe immune-related adverse events, patient's quality of life is not optimal despite a potential longer progression free survival (PFS) benefit (13). As such, the development of novel therapeutic interventions to block melanomagenesis and disease progression to advanced stages will have both high impact and importance.

Ultraviolet radiation (UVR) has been implicated as a major environmental contributor to the development of melanoma. It is well studied that as a carcinogen, UVR can cause the formation of pyrimidine dimers and oxidative DNA base damage such as 8-oxo-7,8-dihydro-2-deoxyguanosine (8-oxo-dG), resulting in genomic mutations. B-raf proto-oncogene (BRAF) is a gene commonly found mutated in melanoma patients (53, 88). However, a study showed that BRAF-mutated melanoma arise early in life at low cumulative UV doses (10). Mutated BRAF is also present in benign and dysplastic melanocytic nevi, suggesting that additional factors may be required for the initiation of melanoma (16). UVR may be an important contributing factor involved in melanomagenesis and disease progression, as many epidemiological studies showed strong association between UVR and risk of cutaneous malignant melanoma (34, 63).

It has been well documented that UVR causes a remarkable increase of nitric oxide (NO) in human skin. NO is an essential signaling molecule participating in many physiological and pathological functions such as vascular dilatation, pigmentation, and macrophage cytotoxicity. Studies also show that NO is an important mediator involved in regulating immune response and T cell proliferation (5).

In recent years, more and more studies revealed the role of NO in tumor development and progression. NO has been shown to inhibit DNA repair through nitrosylation of key repair proteins, which promotes survival of abnormal cells (35). By activating tumor suppressor p53 in response to DNA damage, NO protected melanoma cells against the cytotoxicity of cisplatin (75). NO may also play a role in angiogenesis and metastasis of malignant cells by acting as a potent vasodilator (36). In addition, along with NO and other reactive nitrogen species (RNS), UVR also produces a large amount of reactive oxygen species (ROS) such as superoxide in human skin. The interaction of NO/RNS and ROS produces toxic byproducts such as peroxynitrite, which are genotoxic and interfere with cellular function by causing DNA damage and protein modification, further facilitating melanoma progression (31).

The nitric oxide synthase (NOS) enzymes produce NO from L-arginine and are composed of inducible NOS (iNOS), endothelial NOS (eNOS), and neuronal NOS (nNOS). iNOS generates high levels of NO and regulates processes such as non-specific immune defense. eNOS and nNOS both produce lower levels of NO; while eNOS participates in vascular function such as vasodilation, nNOS, expressed primarily in neural tissue, is involved in central nervous system (CNS) activity. As melanocytes originate from the neural crest and have many gene expression characteristics similar to neural cells (22), nNOS plays a prominent role in regulating NO levels in melanocytes (3). Our studies on patient biopsies have also shown that compared to normal skin, all tested malignant melanomas exhibited markedly higher expression levels of nNOS, which is significantly correlated with disease stage (86). In a recent study reported by Liu et al (2014), elevated nNOS expression in human melanoma tissue was linked to immune dysfunction of circulating T lymphocytes resulting in immunosuppression (46). Studies have also shown that NO scavengers exhibit an antioxidant effect that protects cells from cytotoxic mechanisms (26, 51). Although further mechanistic studies are warranted, this explorative observational study revealed an important role of nNOS-mediated NO signaling in regulating immune response, particularly for human melanoma (46). Accumulating evidence suggests that targeting nNOS signaling may potentially interfere with tumor immune response of melanoma cells.

Preclinical studies showed an enhancement of tumor metastasis potential with IFN-γ exposure, which is consistent in several different model systems as described previously, including melanoma (24, 50). A study in the UVB-HGF/SF transgenic mouse melanoma model, which is derived from by neonatal UV irradiation of hepatocyte growth factor/scatter factor (HGF/SF) (62), demonstrated the direct involvement of macrophage-generated IFN-γ in promoting melanoma growth by inhibiting apoptosis (90). Specific antibodies blocking IFN-γ, but not IFN-α, abolished the UVB-induced melanocyte activation. It is also proposed that depending on the context of micro-environmental factors, the role of IFN-γ may switch from immune-surveillance to immune-editing (92). In fact, an earlier Southwest Oncology Group (SWOG) clinical trial done in 1990, showed that IFN-γ treatment stimulated disease progression in patients with early stage melanoma with more than 50% relapsing or expiring. Although a study in B16 mouse melanoma cells suggested a beneficial effect of IFN-γ in inhibiting metastasis and reducing tumor development (25, 38), the relevance of this mouse model to the human disease is, however, quite weak. Our study contributes to the understanding of melanoma progression by examining the effects of nNOS-NO on IFN-γ-stimulated melanoma progression using specific synthesized nNOS inhibitors.

Signal transducer and activator of transcription (STAT) 1 and 3 are well-documented downstream targets of IFN-γ. Both STAT1 and STAT3 have been found to be involved in the regulation of many genes that contribute to the signaling pathways in melanoma (40) and are considered oncogenes in many cancer types (8, 57). In this study, we will discuss whether the activation of STAT1/3 is associated with the activation of the NO signaling pathway.

Programmed death-ligand 1 (PD-L1) is a transmembrane protein expressed in many cancer cell types, including breast and melanoma, and plays an important role in suppressing the immune system by binding to programmed death receptor-1 (PD-1), causing apoptosis or inactivation of T lymphocytes (94). PD-1 is generally expressed in immune cells such as regulatory T cells (Tregs) and effector T cells, and is upregulated by IL-2 secretion through T cell receptor (TCR) activation. Constitutive PD-1 expression in effector T cells limits autoimmune reactions, while its expression in Tregs prevent excessive inflammation and promotes immune homeostasis (71). PD-L1 has been linked to the ability of melanoma to inhibit T cell responses and evade immune response (37). It has been observed that PD-L1 expression is associated with increased aggressiveness of the disease (7). A study done at UCLA has found that STAT1/3 binding sites are present on the PD-L1 promoter (28). The presence of IFN-γ-secreting $CD8^+$ tumor infiltrating lymphocytes (TILs) in patient tumors strongly correlates with PD-L1 expression (39). The revolutionary new anticancer agents, called checkpoint inhibitors, can target PD-1/PD-L1 signaling and prevent PD-1 from binding to PD-L1, which unleashes the power of a patient's immune system and enhances the ability of T cells to eliminate cancer cells. Recently, studies demonstrated that IFN-γ induces the expression of PD-L1 in human melanoma cells in a NF-kB-dependent manner (29). In addition, another study showed that intratumoral injection of IFN-γ failed to induce signature anti-tumor immune genes (55).

In a transgenic mouse melanoma model, studies have shown that PD-L1 induction may be one of the components by which IFN-γ stimulates melanoma progression (30, 91). The intermittent exposure to sunburn doses of UVR in early life causes mutations in melanocytes and leads to melanoma development if cells carrying the mutations can persistently evade immune surveillance. The inhibitory regulation of NO on T lymphocytes may also contribute to UVR-induced immunosuppression in human (32, 66). Given this, it stands to reason that NO may be the messenger between IFN-γ and PD-L1-mediated immune checkpoint.

To date, the underlying molecular mechanisms of IFN-γ-mediated pro-tumorigenesis have not been well-defined. Accumulating evidence indicates that IFN-γ may alter the immune microenvironment of melanoma cells either directly by the nNOS/NO pathway or indirectly by potentializing PD-L1-mediated immune inhibition. Our study focuses on demonstrating the underlying mechanisms of IFN-γ-stimulated melanoma progression and developing novel pharmaceutical inhibitors targeting the IFN-γ-mediated signal pathway for melanoma prevention and therapy. Completion of our studies will not only enhance our fundamental understanding of melanoma pathogenesis, but also will lead to the development of pharmacological treatments that complement existing immunotherapy with FDA approved checkpoint inhibitors.

Results

IFN-γ stimulates melanoma progression via activation of nNOS-NO signaling. Utilizing metastatic melanoma A375 cells, we determined the effect of IFN-γ on melanoma invasion potential. As shown in FIG. 1A, IFN-γ significantly enhanced melanoma invasion potential compared to control (p<0.05). The adhesion capacity of melanoma cells to fibroblast cells was also significantly enhanced by IFN-γ (FIG. 1B), indicating the gain of metastatic potential (56).

Figure 2:
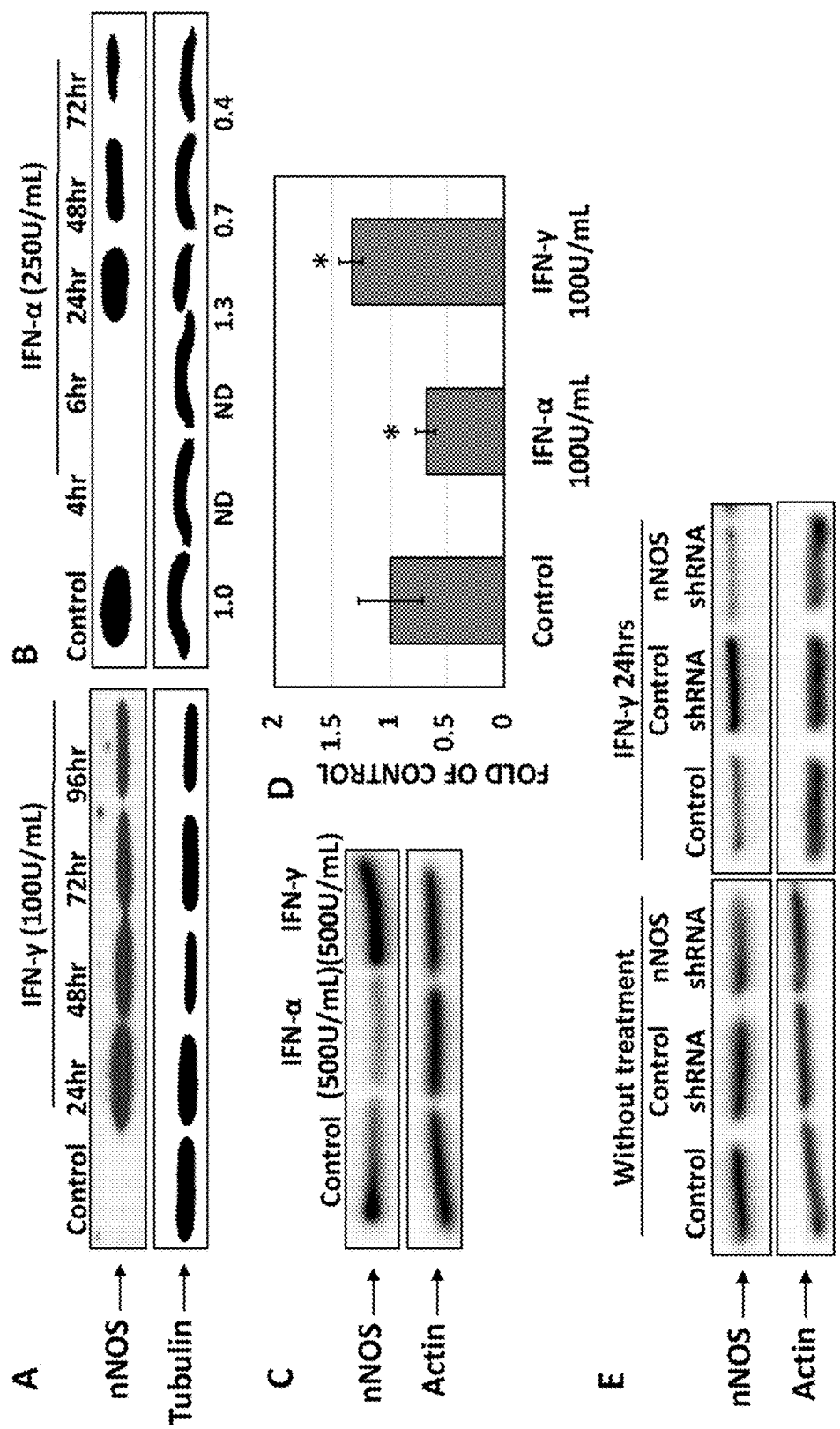
FIG. 2. A-C) Effects of IFN-α and IFN-γ treatment on nNOS expression levels in human primary melanoma WM3211 cells (A-B) and metastatic melanoma A375 cells. C) Distinct effects of IFN-α and IFN-γ on nNOS expression of A375 metastatic melanoma cells. A375 cells were treated with 500 units/mL of IFN-α or IFN-γ for 48 hours and whole cell lysates were collected. Samples were subjected to Western blot analysis for nNOS. A control of the protein loading was performed by detecting actin. D) Intracellular nitric oxide levels detected by microplate reader using DAF-FM fluorescence probe after IFN-α or IFN-γ treatment for 24 hours. E) IFN-γ-inducible nNOS expression was abrogated in nNOS-depleted melanoma cells. A375 cells transfected with shRNA-nNOS were treated with IFN-γ for 24 hours, followed by Western blot analysis.

As shown in FIG. 2A, IFN-γ markedly induced nNOS expression levels in primary melanoma WM3211 cells, which persisted even after 96 hours. In contrast, the expression of nNOS rapidly dropped to undetectable levels after IFN-α treatment within 4 hours, which was then recovered by 24 hours (FIG. 2B). The same pattern was also evident in a different cell line, A375 cells, when exposed to IFN-α and IFN-γ (FIG. 2C). Primary melanoma WM3211 cells are more sensitive to IFN-γ treatments in comparison to metastatic A375 cells; the induction of nNOS was observed at as low as 100 units/mL. In parallel with increased nNOS expression, elevated intracellular NO levels were also detected using DAF-FM fluorescence probe after exposure to IFN-γ. However, in melanoma cells treated with IFN-α, NO production was significantly decreased (FIG. 2D), which is consistent with the reduced nNOS expression after IFN-α treatment (FIGS. 2B and 2C). Knockdown of nNOS by shRNA-nNOS markedly abrogated the induction of nNOS by IFN-γ treatment for 24 hours in A375 cells (FIG. 2E).

Figure 3:
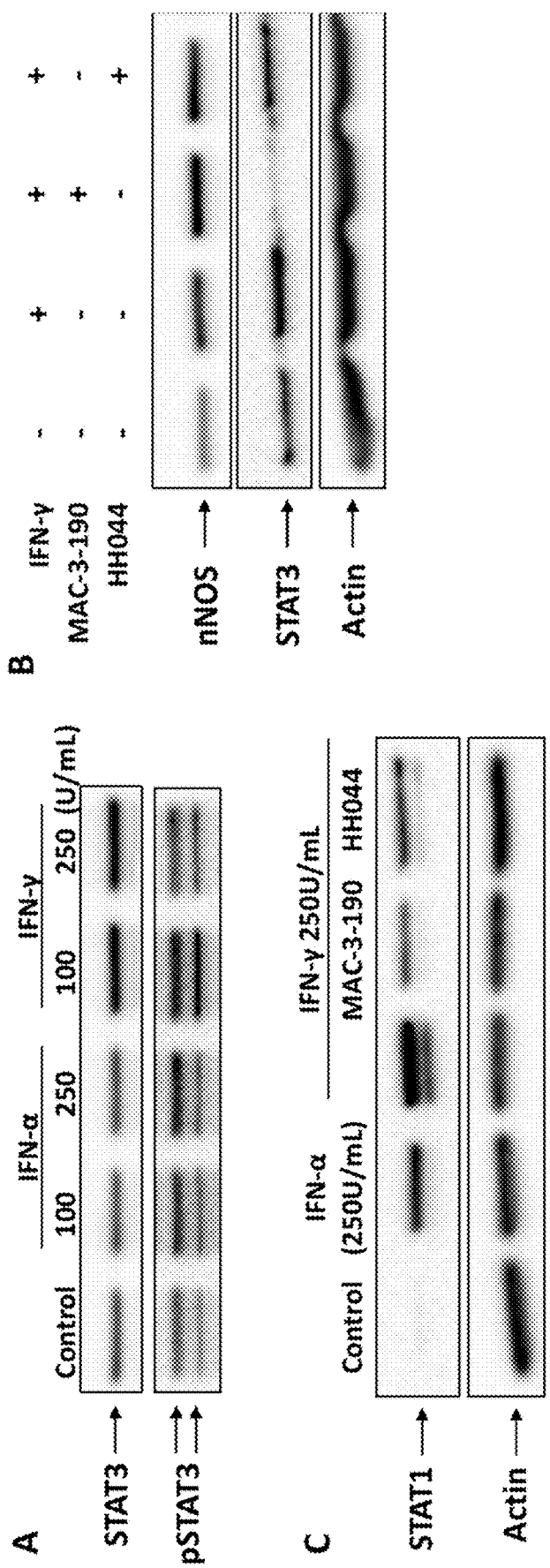
FIG. 3. A) Effects of IFN-γ on STAT3 and phosphor-STAT3 expression levels in melanoma. A375 cells were treated with 100 units/mL and 250 units/mL of IFN-γ or IFN-α for 24 hours; whole cell lysates and nuclear extracts were used for Western blot analysis to detect STAT3 and pSTAT3 respectively. Specific nNOS inhibitor MAC-3-190 (3 μM) inhibited the activation of B) STAT3 and C) STAT1 induced by IFN-γ in A375 cells. A375 metastatic melanoma cells were treated with IFN-γ with or without MAC-3-190 for 48 hours.

As a downstream target of IFN-γ and an important transcription factor of PD-L1 expression (54), the expression levels of STAT3 were increased to 1.6-folds of control when cells were exposed to IFN-γ. Phospho-STAT3 levels were also induced to 1.9-folds of control, suggesting that IFN-γ treatment was associated with activation of STAT3-mediated signaling (FIG. 3A). Interestingly, nNOS inhibitors, MAC-3-190 and HH044, failed to inhibit the IFN-γ inducible nNOS, but MAC-3-190 at 3 µM effectively diminished the induction of STAT3 expression activated when cells were co-treated with IFN-γ (FIG. 3B). Though IFN-α was observed to increase the expression of STAT1, IFN-γ exhibited a higher induction of STAT1, which was also effectively diminished when co-treated with nNOS inhibitors (FIG. 3C).

Figure 4:
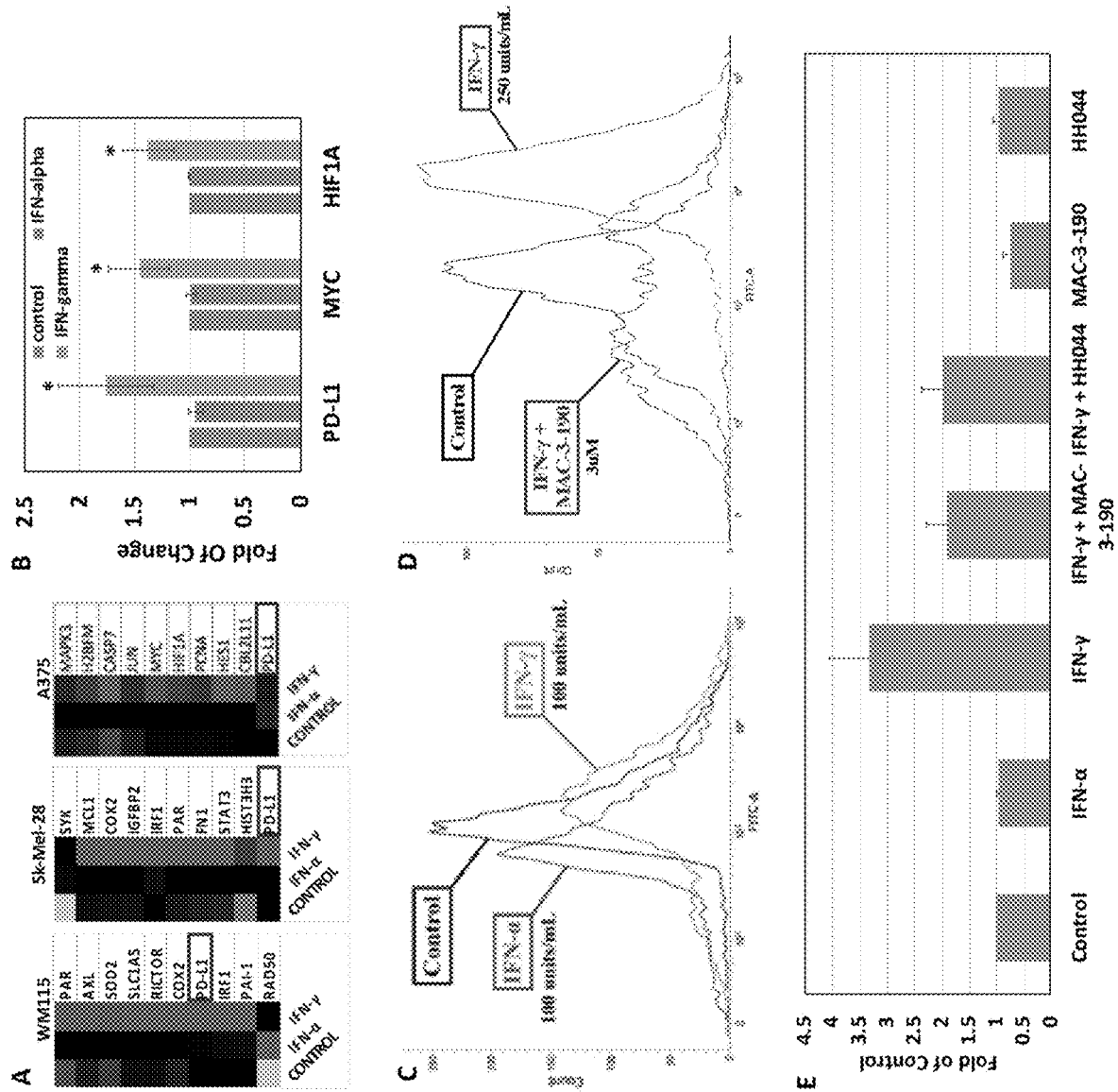
FIG. 4. A) Heat map of Reverse Phase Protein Array (RPPA) showing distinct effects of IFN-α and IFN-γ on protein expression levels in three human melanoma cell lines (WM115, Sk-mel-28 and A375). Three melanoma cell lines were treated with 250 units/mL of interferons for 48 hours. Whole cell lysates were collected and subjected to RPPA assay. The top 10 upregulated proteins by IFN-γ were selected from 302 proteins and phosphorylation of key signaling molecules. Red, high expression; green, low expression. All the data points were normalized for protein loading and transformed to linear value. B) PD-L1, c-Myc and HIF1α were significantly induced by IFN-γ. Average changes of three cell lines detected by RPPA were shown in the figure. *, $p<0.05$ in comparison to control and IFN-α. C-E) Induction of PD-L1 by IFN-γ was diminished by the co-treatment of nNOS inhibitors. A375 melanoma cells were exposed to IFN-α or IFN-γ with or without nNOS inhibitor MAC-3-190 or HH044 (3 μM) for 72 hours. Cell surface expression of PD-L1 was determined by flow cytometry. Representative histograms out of two independent experimental replicates are shown. C) IFN-α or IFN-γ (100 Units/ml); D-E) IFN-α or IFN-γ (250 Units/ml).

The induction of PD-L1 expression by IFN-γ was diminished by nNOS inhibitor treatments. In our study, we also used RPPA to assess the effects of IFN-α and IFN-γ on the major growth and survival signaling molecules in three human melanoma cell lines (FIG. 4A). Consistent with a recent study (29), IFN-γ treatment significantly up-regulated PD-L1 expression compared to control. Increased c-Myc and HIF-1α expression levels were also evident after IFN-γ treatment (FIG. 4B), which are associated with tumor metastasis and poor prognosis in melanoma patients (33, 45).

Up-regulation of PD-L1 by IFN-γ was confirmed using flow cytometry (FIG. 4C). Our data showed that IFN-γ increased cell surface expression of PD-L1 in all three cell lines examined via flow cytometry, while IFN-α at the same concentration reduced the PD-L1 expression. Of note, nNOS inhibitor, MAC-3-190, significantly reversed the induction of PD-L1 by IFN-γ after 72-hour treatment (FIG. 4D); the MFI of PD-L1 staining obtained via flow cytometry was reduced from 3.3-folds of control to 1.9-folds of control (FIG. 4E).

Figure 5:
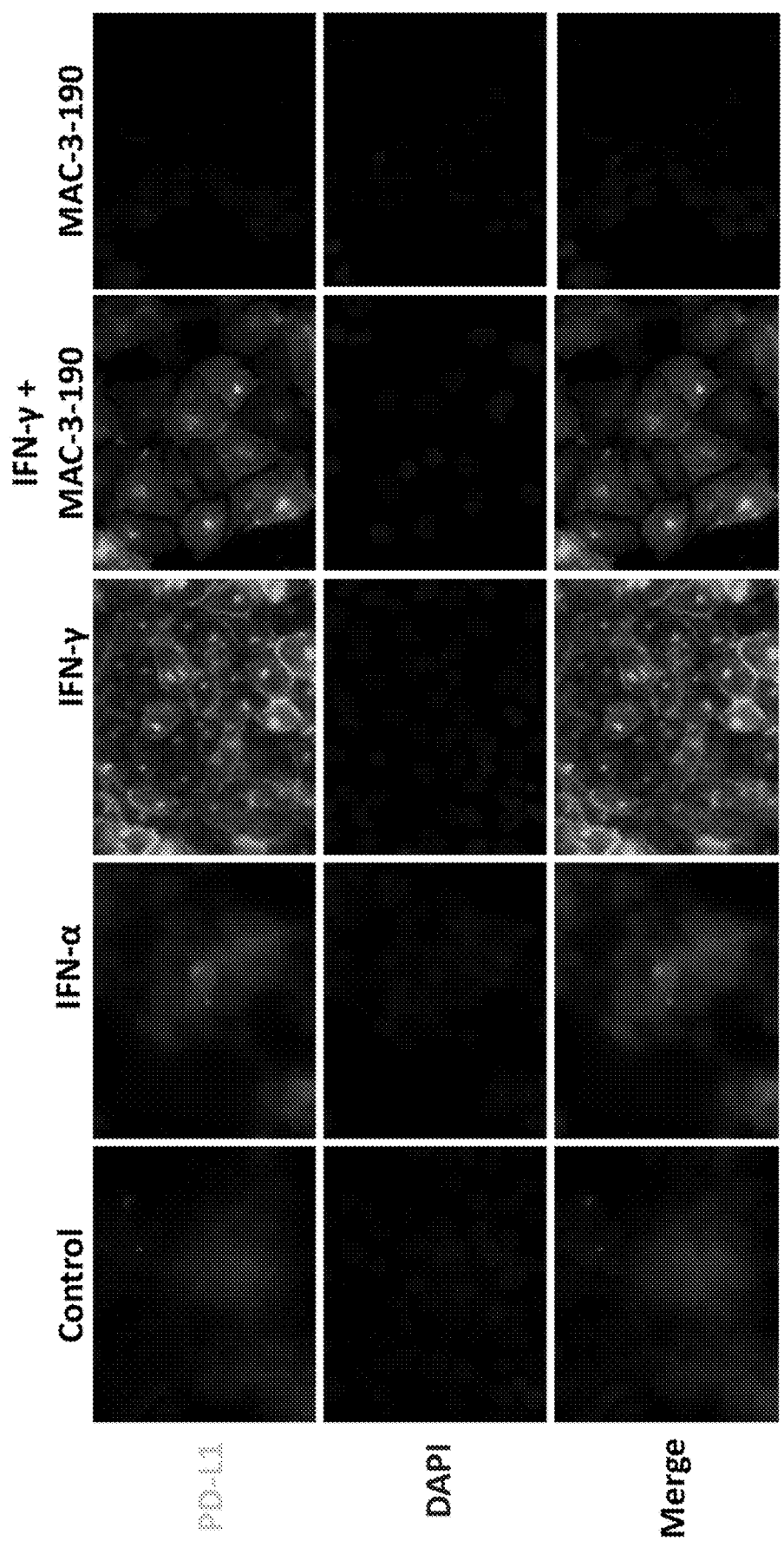
FIG. 5. Expression of PD-L1 in metastatic melanoma A375 cells detected by immunofluorescence staining. A375 cells were plated on coverslips and allowed to adhere overnight to 75% confluence then treated with IFN-α or IFN-γ (250 Units/ml) with or without MAC-3-190 (304) of 72 hours. Cells were then fixed and permeabilized with 4% formaldehyde and methanol. Samples were blocked in blocking buffer containing 5% horse serum for 1 hour. The slides were then allowed to incubate in a 1:50 PD-L1 antibody dilution overnight at 4° C. and DAPI reagent for 1 hour. Representative images are shown stained with PD-L1 antibody (green) and DAPI (blue fluorescence). (Original magnifications, 100×). Representative images for 2 experimental replicates are shown.

In images obtained from immunofluorescence microscopy, control and IFN-α treated cells showed low basal expression of PD-L1. After IFN-γ treatment, however, the extracellular expression of PD-L1 was markedly induced in melanoma cells as indicated by the intense green fluorescence staining. Co-treatment with 3 µM of MAC-3-190 significantly diminished the IFN-γ-inducible PD-L1 expression, while treatment with MAC-3-190 alone did not alter the basal level of PD-L1 compared to that of control (FIG. 5).

Figure 6:
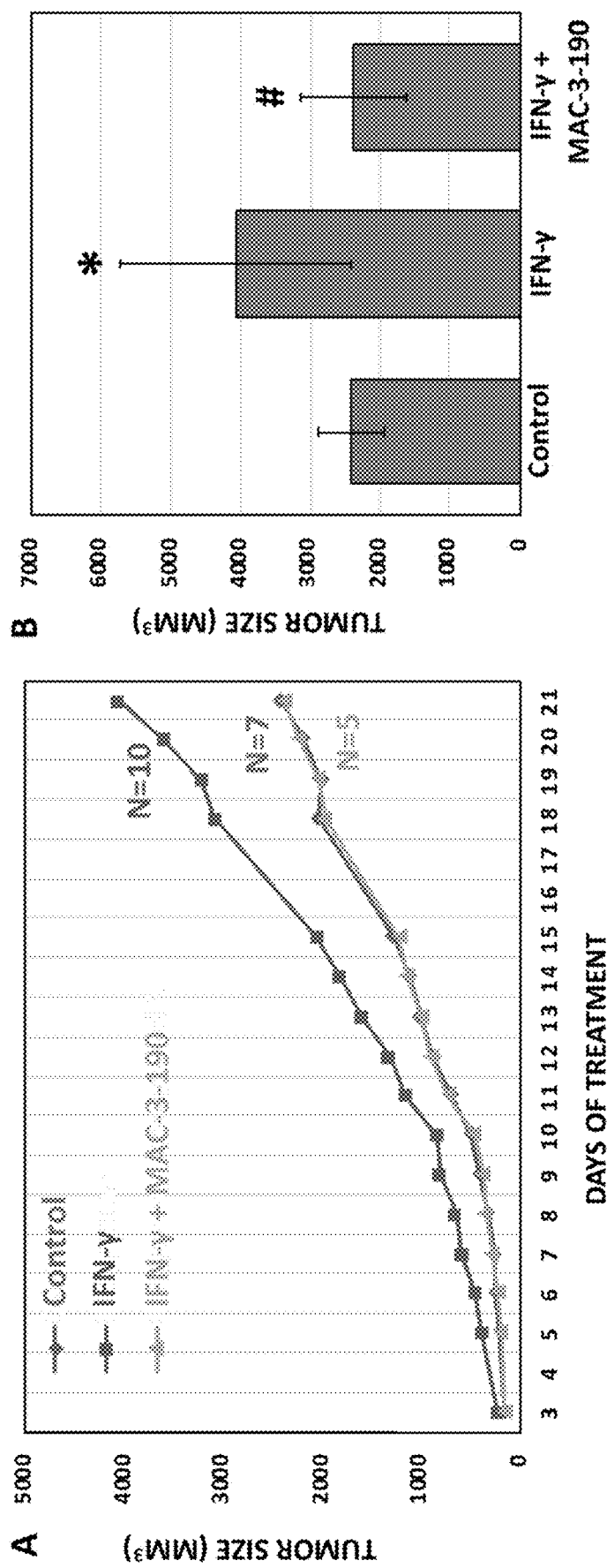
FIG. 6. Promising anti-melanoma activity of novel nNOS inhibitors. A-B) nNOS inhibitor MAC-3-190 (5 mg/kg, i.p daily) diminished the tumor growth stimulated by IFN-γ (1000 units, i.p daily). *, $p<0.05$ compared to control; #, $p<0.05$, compared to IFN-γ treatment. B) nNOS inhibitor HH044 (10 mg/kg, i.p daily) markedly inhibited the tumor growth of human melanoma in vivo compared to control. C) HH044 significantly decreased the final mass of xenograft tumors with no significant change in lung and body weight. *, $p<0.05$ compared to control. D) PD-L1 expression of HH044 treated tumors was significantly decreased as detected by flow cytometry. *, $p<0.05$ compared to control. Metastatic melanoma A375 cells were injected to nude mice subcutaneously on the flank. The growth of tumor was measured daily and tumor volumes were determined using digital calipers (Fisher Sci) by using the formula tumor volume $(mm^3)=[Length\times(Width^2)]/2$. Data was represented as mean±SD. E) Single cell suspensions of harvested tumors were stained with Alexa Fluor 488 conjugated PD-L1 antibody and PD-L1 expression was determined via flow cytometry.
Figure 6:
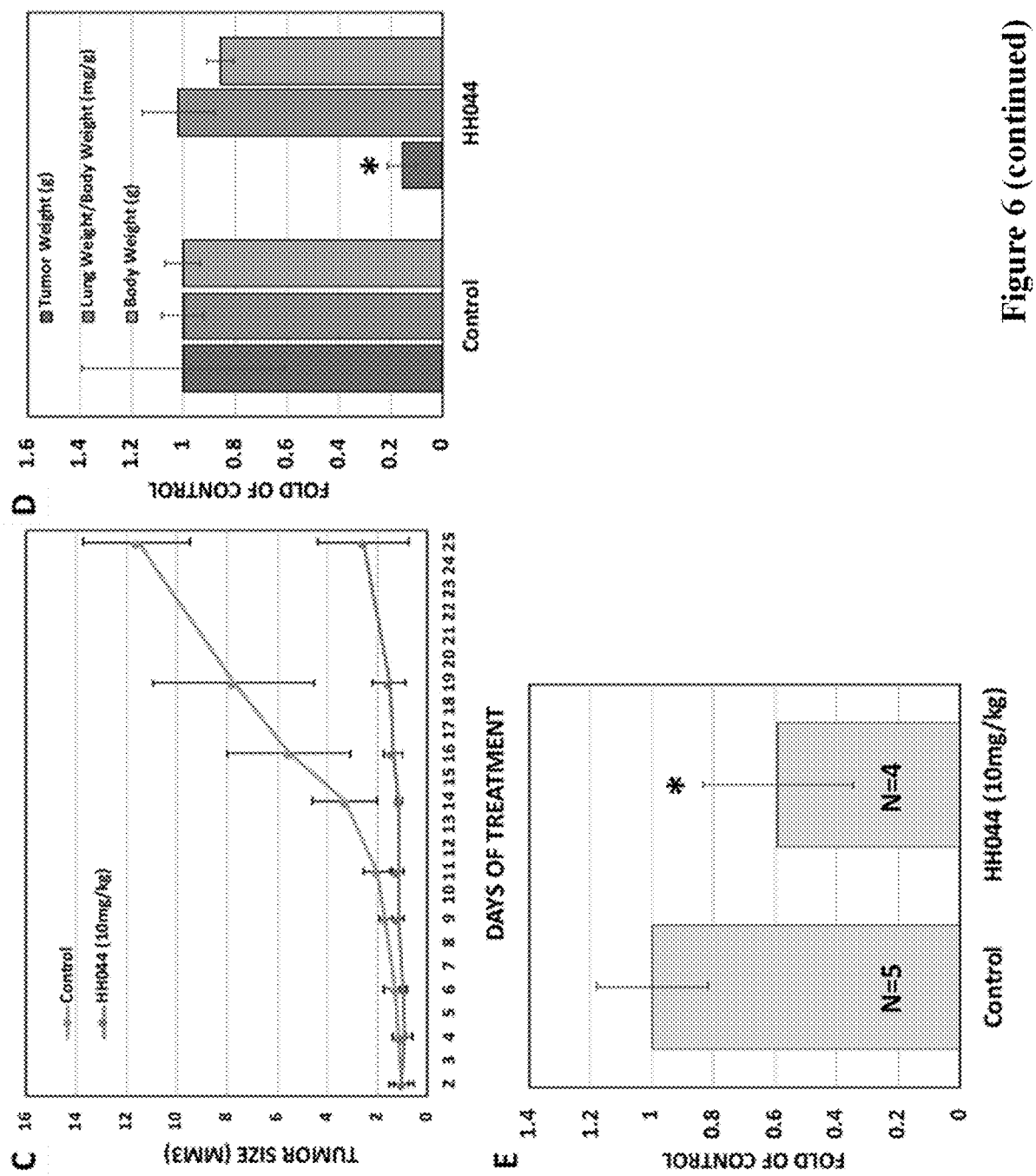

Taken together, these results are consistent with our hypothesis that IFN-γ sustained a more aggressive phenotype of melanoma cells via activation of nNOS-NO signaling; novel nNOS inhibitors efficiently abrogated the activation of STAT1/3 and the induction of PD-L1 expression by IFN-γ treatment.

nNOS inhibitors suppressed tumor growth in the presence of IFN-γ in a xenograft mouse model. In our study, the newly developed nNOS inhibitors exhibited potent anti-melanoma activity both in vitro (Table 1) and in vivo (FIG. 6). As listed in Table 1, the $IC_{50}$s of all candidate compounds are less than 10 µM, which are comparable or even more potent in comparison to that of chemotherapeutic drug cisplatin (4.2 µM and 14.3 µM in A375 and Sk-mel-28 cells, respectively). Notably, the inhibition by nNOS inhibitors is more predominant in metastatic melanoma A375 cells compared to primary early stage WM3211 cells, which supports our hypothesis that nNOS/NO signaling is more critical to melanoma progression than in the initiation phase.

Table 1. Novel potent and highly selective nNOS inhibitors. All the NOS isozymes used were recombinant enzymes overexpressed in *E. coli*. Ki values are calculated directly using known literature methods and detailed in co-PI R. Silverman's published manuscripts (17, 18, 64, 85). Cytotoxic effects of nNOS inhibitors in human melanoma were detected by MTT colorimetric analysis (85). The $IC_{50}$ values are the average of at least two human melanoma cell lines.

| Compounds | Ki(uM) | | | Selectivity | | Cytotoxicity ($IC_{50}$ from 3 melanoma cell lines) |
|---|---|---|---|---|---|---|
| | nNOS | iNOS | eNOS | nNOS/iNOS | nNOS/eNOS | |
| HH044 | 0.005 | 1.56 | 2.48 | 312 | 495 | 5.27 ± 3.3 µM |
| MAC-3-190 | 0.033 | 4.54 | 6.09 | 138 | 184 | 1.21 ± 0.19 µM |

Selectivity of nNOS over iNOS or eNOS was calculated as described previously.
A375: human metastatic, $BRAF^{V600E}$;
Sk-Mel-28: human metastatic, $BRAF^{V600E}$
wm3211: human primary, $BRAF^{wt}$ Using a melanoma xenograft tumor model, our animal study showed that IFN-γ treatment (1000 units/day) significantly stimulated tumor growth in vivo (FIG. 6A). As shown in FIG. 6B, co-treatment with MAC-3-190, a water soluble potent nNOS inhibitor, effectively diminished the induction in tumor volume by the end of study (p<0.05 compared to IFN-γ treatment). The efficient dose of MAC-3-190 was as low as 5 mg/kg subcutaneously injected daily.

We further determined the in vivo effects of nNOS inhibitor HH044 in tumor growth. Treatments with HH044 (10 mg/kg i.p for 21 day) significantly reduced the tumor growth with no apparent systemic toxicities observed (FIG. 6C). As shown in FIG. 6D, it was also found at the end of the study that the mass of the tumor treated with HH044 was reduced with no significant changes in lung and body weight (p<0.05 compared to that of control). Analysis of single cell suspensions obtained from xenografted tumors showed a significant decrease of PD-L1 expression levels in HH044-treated mice in comparison to control group (FIG. 6E, p<0.05).

Figure 7:
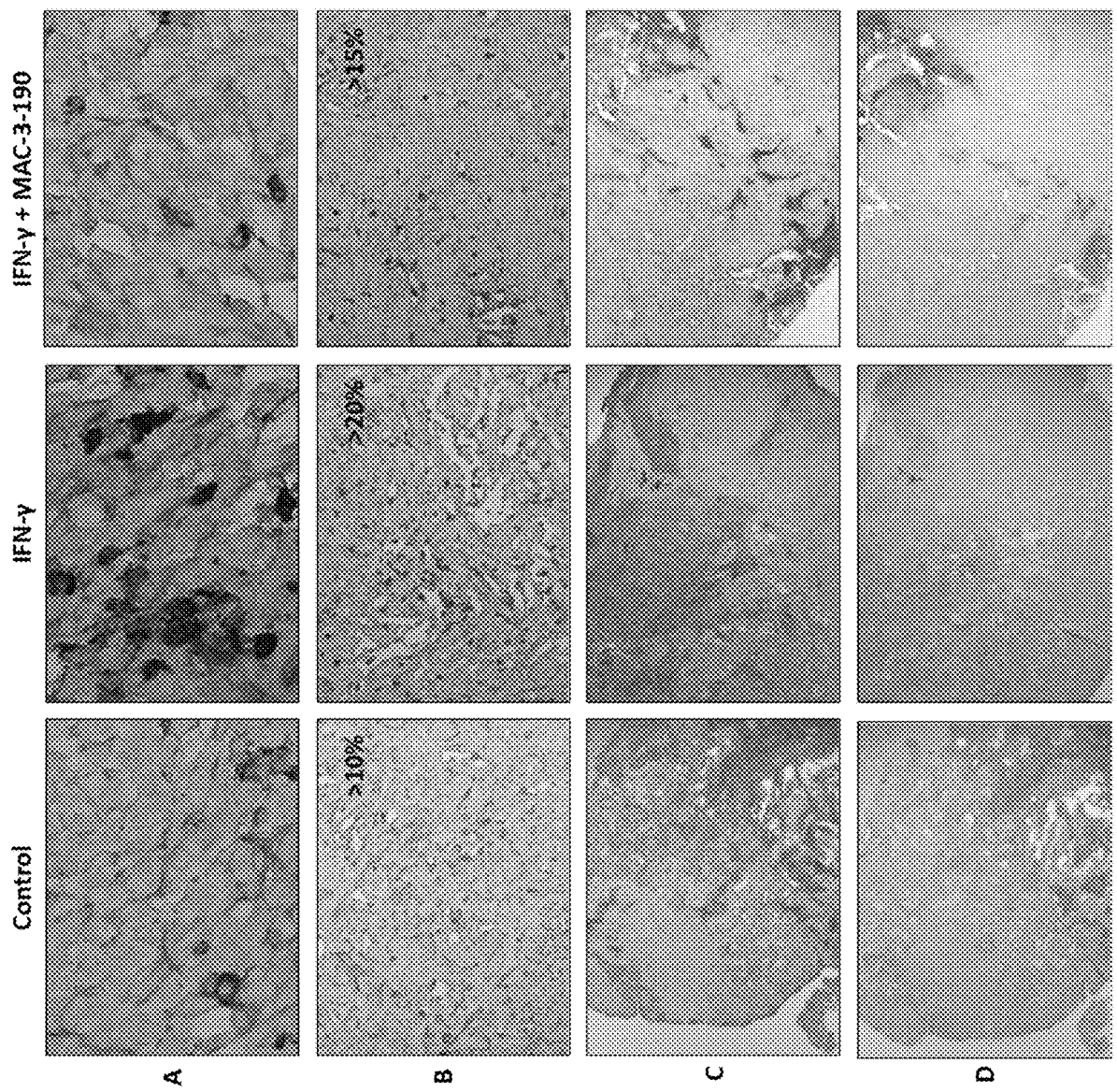
FIG. 7. Expression of PD-L1 in xenograft tumor samples obtained from the subject is administered an inhibitor of NOS and further is administered study detected by immunohistochemistry staining. PD-L1 staining (brown) of specimens at 100× (A) and 20× (B) magnification. Images were captured in CD8-negative areas for control and IFN-γ with or without MAC-3-190 treated tumors. PD-L1 (C) and CD8 (D) stained specimens captured at 2× magnification. Specimens were fixed in a 10% formalin solution and embedded in paraffin wax for automatic processing using the Ventana Benchmark Ultra machine.

PD-L1 expression elevated in CD8-negative melanoma tumor when treated with IFN-γ. As shown in FIG. 7, the positive staining of PD-L1 in control A375 xenograft tumors was >10%, which is elevated to >20% after 21-day treatment of IFN-γ (1000 units per mouse, i.p. daily). The co-treatment with MAC-3-190 effectively decreased PD-L1-positive staining to >15%, suggesting a role of nNOS activity in regulating PD-L1 expression in vivo (FIGS. 7A and 7B). At 2× magnification, it is evident that areas positive with CD8+ staining (FIG. 7D) also stain strongly positive for PD-L1 (FIG. 7C). After treatment with IFN-γ, PD-L1 positive staining was also evident in CD8-negative tissues, which suggests that the induction of PD-L1 was independent with the presence of tumor infiltrated lymphocytes (TILs) and might be stimulated by IFN-γ directly. This effect appears to be effectively blocked with the co-administration of MAC-3-190 (5 mg/kg/day).

Discussion

Figure 8:
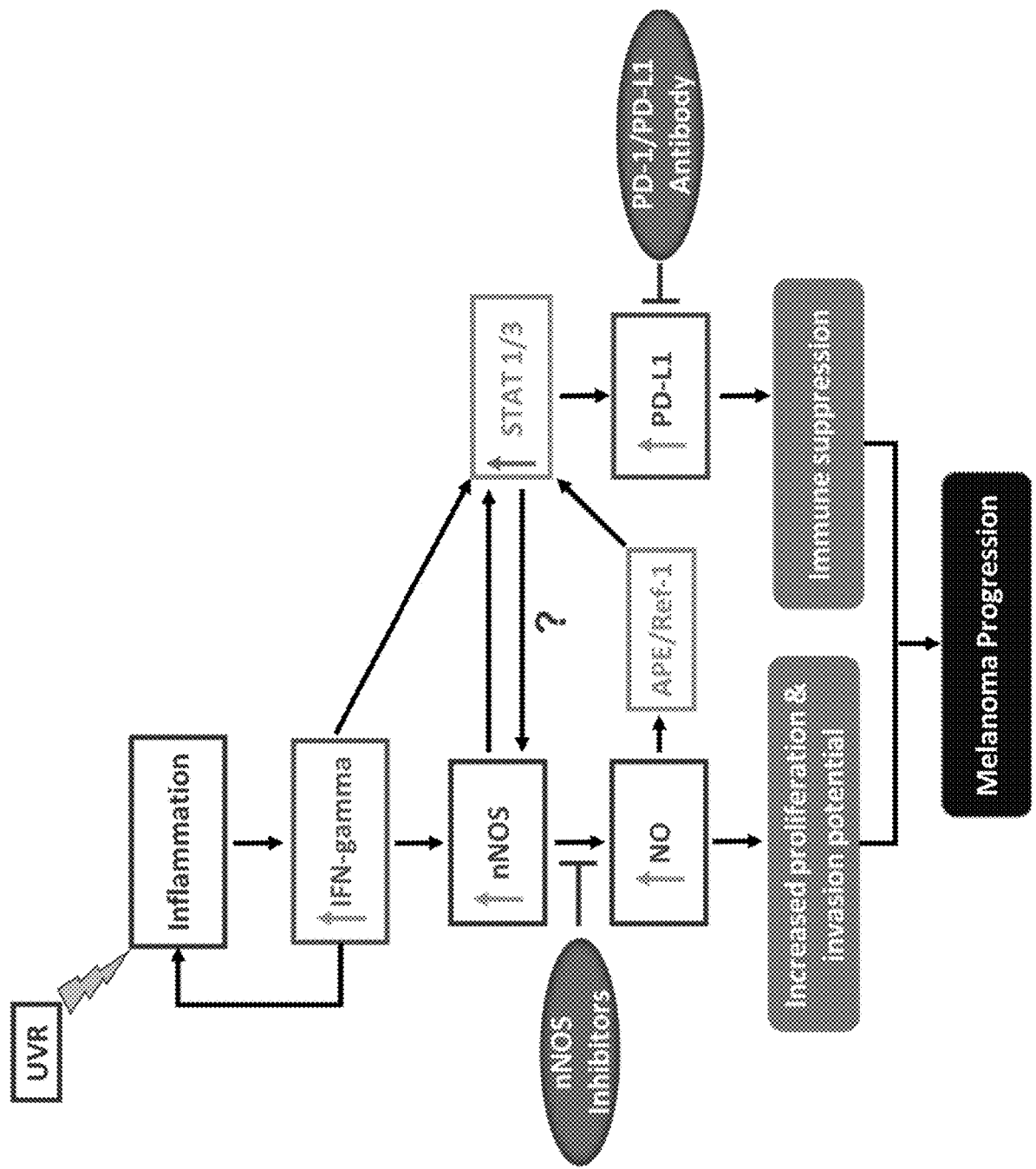
FIG. 8. nNOS plays a central role in interferon-γ-mediated melanoma progression. UV radiation especially at sunburn dosage causes damages to the skin and stimulates the production of IFN-γ. IFN-γ is shown to promote inflammation, melanomagenesis and disease progression both in transgenic mouse model (90) and melanoma patients (58). Our study showed that IFN-γ triggers the activation of nNOS-NO signaling cascades associated with the activation of nuclear transcription factor, STAT3. Abnormally high levels of NO fuels melanoma proliferation and facilitates cancer cells escape from immune surveillance by inducing the expression of PD-L1, which negatively regulates T cells responses to tumor cells. nNOS inhibitors not only effectively reduce the production of NO, but also inhibit IFN-γ-stimulated PD-L1 expression and the activation of STAT1/3 signaling. Both in vitro and in vivo study demonstrated that targeting nNOS-NO using small molecular inhibitors is a promising strategy for melanoma therapy.

Our study, for the first time, demonstrates the critical role of nNOS-mediated NO signaling in IFN-γ-stimulated melanoma progression both in vitro and in vivo (FIG. 8). By inhibition of nNOS using novel small molecular inhibitors, we have successfully inhibited melanoma metastasis potential and the induction of PD-L1 stimulated by IFN-γ treatment. Our data also showed that co-treatment with nNOS inhibitors has effectively alleviated the production of NO and the activation of STAT1- and STAT3-signaling after IFN-γ exposure. Consistently, our in vivo studies demonstrated that using nNOS inhibitor, MAC-3-190, effectively suppressed melanoma tumor growth stimulated by IFN-γ in a melanoma xenograft mouse model. Our study in combination with accumulating evidence indicates that targeting nNOS-mediated NO signaling using small molecular inhibitors may be a novel and effective strategy for melanoma therapy.

Distinct from IFN-γ, IFN-α has been extensively utilized in the clinic as adjuvant treatment for melanoma patients who are considered to be at high risk of relapse after surgical resection. IFN-α exerts its anti-tumor effects via different mechanisms including immunoregulation, shifting host immunity from a Th2 predominant response to a Th1 response (2), resulting in improved disease-free survival (20, 23). In a genetically engineered mouse melanoma model, targeted activation of IFN-α in combination with blockade of PD-1 was shown to prolong survival significantly (9). Our studies show that IFN-α reduces nNOS expression to undetectable levels from 4 to 6 hours of treatment, but the expression was recovered by 24 hours. With prolonged treatment, the nNOS expression levels at 96 hours are reduced compared to control. This suggests that there may be an adaptive mechanism that recovers nNOS expression, though the inhibiting effects of IFN-α persist as treatment continues.

IFN-γ, produced mainly by natural killer (NK) cells and natural killer T (NKT) cells as part of the innate response, before antigen-specific immunity develops, is crucial for immune response (68). Secreted IFN-γ mediates the function of antigen presenting cells (APCs), inhibits Th2 cell development and promotes the differentiation of Th1 cells which further increases IFN-γ secretion (77). Studies of heathy individuals have shown that with exposure to UV radiation, serum IFN-γ levels are significantly elevated and remain elevated for several weeks (47). It was reported that in hepatocellular carcinoma, low blood serum level of IFN-γ is a predictor of disease recurrence (44). However, in recent years, more and more studies revealed the distinct pro-tumorigenic activity of IFN-γ in human melanoma.

In the event of a sunburn, macrophages are recruited to the area and secret IFN-γ, which may alter the microenvironment of cancer cells (70). In a UVB-HGF/SF transgenic mouse model, blocking IFN-γ effectively abolished macrophage-enhanced melanoma growth and survival (90). Even though IFN-γ-mediated NO production by macrophages plays a pivotal role in the protective immunity against microbial pathogens (52), earlier murine studies showed that T-cell-derived IFN-γ activates the production of NO which suppresses T cell proliferation by initiating a cycle of macrophage activation (4, 81). Consistently, other studies showed that the upregulation of NO was associated with immune suppression (79), which may, at least partially, contribute to UV-induced local immunosuppression (65) and subsequently facilitate its stimulation of cell proliferation and invasion potential observed in cancers (31, 85).

Lollini's group showed that IFN-γ treatment generated a significant increase of tumor metastasis independent of its anti-proliferative effect in mouse melanoma with an approximately 20-fold increase in the number of lung metastasis despite a 99% inhibition of cell growth in vitro (49). Our study also observed that IFN-γ significantly increased the invasion and metastatic potential of melanoma cells (FIG. 1). Consistently, another recent study showed that IFN-γ enhances the expression of CD74 known as a major histocompatibility complex class II-associated invariant chain, which interacts with its ligand and thereby activates the PI3K/AKT pathway in melanoma, leading to the promotion of tumor survival and growth (74). This remarkable pro-tumorigenic activity of IFN-γ in human melanoma was also observed in a Phase III clinical trial, which showed that adjuvant treatment with daily subcutaneous injection of IFN-γ did not improve disease-free survival or overall survival of patients with high-risk CM resected with curative intent, constituting strong evidence against any clinically beneficial application (59). The molecular mechanisms of IFN-γ-mediated pro-tumorigenic effects, however, are not yet fully understood. The distinct responses of IFN-γ in melanoma compared to other tumors suggest that IFN-γ might activate a unique signaling pathway, facilitating the progression of disease.

As shown in our study, we found that IFN-γ treatment predominantly induced nNOS expression in primary melanoma cells, while the same dose of IFN-α markedly reduced nNOS levels. Consistently, detected intracellular NO levels correlated with nNOS expression levels and were increased after exposure to IFN-γ. The effects of IFN-α and IFN-γ on regulating nNOS-NO signaling may help to explain the distinct clinical responses of the two isotype IFNs in melanoma patients, which also provides new insight into the pathogenesis of IFN-γ-stimulated melanoma progression. Furthermore, we have identified a novel mechanism of nNOS-NO signaling in PD-L1-mediated immunosuppression of human melanoma. nNOS inhibitors have effectively reversed the induction of PD-L1 by IFN-γ in melanoma cells. Further, our in vivo study showed that nNOS inhibitor, MAC-3-190, significantly reduced PD-L1 expression in xenograft tumors even at a low dose of 10 mg/kg/day. The important role of nNOS-NO signaling in IFN-γ-stimulated melanoma progression and PD-L1-mediated immunosuppression provides a unique strategy for adjuvant treatment of melanoma by targeting the IFN-γ-nNOS-NO-PD-L1 signaling axis (FIG. 8).

Apurinic/apyrimidinic endonuclease-1/redox factor-1 (APE/Ref-1), a multiple function protein which was first recognized as DNA endonuclease, is found to regulate many nuclear transcription factor activities both in a redox-dependent and redox-independent manner (82). Our previous studies demonstrated that in human melanoma, over-activated APE/Ref-1 is sensitive to redox disequilibrium, and plays an important role in disease progression and the development of drug resistance by possessing DNA repair and redox regulatory activities (82, 83). In addition to ROS, NO activates APE/Ref-1 in a feedforward manner, which leads to constitutive overexpression of APE/Ref-1 in melanoma cells (87). In an earlier pancreatic cancer study, researchers demonstrated that STAT3 transcriptional activity is directly regulated by APE/Ref-1 activity (14), and that may be the result of their formation of an inducible complex (67).

As downstream targets, transcription factors STAT1 and STAT3 are well-known to be regulated by IFN-γ. When IFN-γ binds to JAK1 and JAK2 receptors, the STATs are activated subsequently by phosphorylation, which allows the STAT dimers to translocate into the nucleus binding to gamma-activated sequences (GAS). The distinct pattern of the activated genes may re-direct signals in the cell and cause biological changes subsequently, such as tumorigenesis (8). In general, STAT1 was considered as a tumor suppressor (8), but there is growing evidence showing that over-activated STAT1 can also act as a tumor promotor (12). Knockdown STAT1 in melanoma was shown to slow the migration and invasion potential both in vitro and in vivo (69). On the contrary, the activation of STAT1 in immune cells activates the immune response to melanoma (72).

STAT3 has been extensively studied in many cancer types, including melanoma and has been implicated in the regulation of many genes that contribute to the signaling pathways in melanoma survival and proliferation (8, 40). Activated STAT signaling in human tumors have been well documented, and in recent years, researchers are developing molecular and pharmacological strategies targeting STAT3 signaling for therapeutic interventions.

Our study showed that both the expression levels and the activity of STAT1/3 were increased after IFN-γ treatment, which was abolished by the co-treatment with MAC-3-190 and HH044. Our data suggests that nNOS-NO signaling may play an important role in IFN-γ-activated STAT1/3 signaling. Targeting nNOS might effectively block tumor progression by inhibiting the IFN-γ-activated STAT1/3 axis involved in melanoma proliferation and metastasis.

Our RPPA results showed that IFN-γ treatment induced the expression of genes associated with poor prognosis and disease progression in melanoma patients such as PD-L1, c-Myc, and HIF1α (15, 41, 45, 48). Of note, our data demonstrated that the induction of PD-L1 by IFN-γ was dose-dependent, indicating a direct regulation mechanism may be involved. In recent years, accumulating evidence indicates that IFN-γ may alter the microenvironment of cancer cells, which allows them to escape from immune response. This effect may, in part, be mediated by the suppression of T lymphocyte proliferation by NO (5, 32, 66, 81).

PD-L1 expressed on the surface of cancer cells engages PD-1 on T cells and subsequently triggers inhibitory signaling downstream of the T cell receptor (TCR) (29, 78). In recent years, more and more studies demonstrate the critical role of IFN-γ in melanoma immunity via upregulating PD-L1 expression, fostering an immune-suppression microenvironment (28, 60). Ribas' group at UCLA found that the regulation of PD-L1 expression is through the JAK1/2-STAT1/3-IRF1 axis (28). As a primary inducer of PD-L1 expression (29, 74), IFN-γ was detected at the interface of PD-L1$^+$ tumors and tumor infiltrating lymphocytes (TIL), suggesting that TILs trigger their own inhibition by secreting cytokines such as IFN-γ that drive tumor PD-L1 expression (76). A recent study has found that older melanoma patients may have a better response rate to anti-PD-1 immunotherapy due to a higher population of regulator T cells (Tregs) to cytotoxic T lymphocytes (CTLs) compared to younger patients (42). This suggests that the higher population of Tregs, which have anti-proliferative and anti-inflammatory properties, may suppress the activity and expansion of CD8$^+$ CTLs (71). Though IFN-γ was found to be a CTL chemoattractant that increases CTL cytotoxic function and motility (11), melanoma cells have acquired the ability to hijack the IFN-γ signaling pathway to upregulate PD-L1, thus escaping immune response. Consistently, our xenograft tumor samples stained with CD8 and PD-L1 showed that melanoma cells exhibited higher PD-L1 expression levels in the areas with more CD8+-TILs present. The PD-L1 expression in areas of the tumor that are negative with CD8$^+$ staining, was also elevated with IFN-γ treatment. Our study also showed that co-treatment with MAC-3-190 reduced the expression of IFN-γ-inducible PD-L1 in xenograft tumors. A limitation in our study is the lack of forkhead box P3 (FoxP3) staining to determine the ratio of Tregs to CD8$^+$ CTLs, which is currently underway.

A recent mechanistic study showed that in human melanoma cells, PD-L1 expression was primarily regulated by the IFN-γ-activated JAK1/JAK2-STAT1/STAT2/STAT3-IRF1 axis (28). Similar mechanisms were also defined in a head and neck cancer study (19). Such adaptive induction of PD-L1 in response to IFN-γ represents a novel mechanism by which cancer cells attempt to protect themselves from immune-cell mediated killing (78). More recent studies showed that a loss-of-function mutation of IFN-associated JAK signaling results in acquired resistance of PD-L1 blockade with a lack of response to IFN-γ-induced PD-L1 (6, 28, 93). Thus, a detailed understanding of signaling pathways regulating the induction of PD-L1 may help to improve the immunotherapy of cancer.

Developing a small molecule to rescue immune response in cancer patients has attracted increasing attention among cancer researchers due to their many advantages. Small molecules, unlike biologics, are more stable and may be administered orally and due to their smaller size, they may also offer prospects of intracellular exposure in the tumor microenvironment. There are also lower costs associated with the production, preparation and drug delivery of small molecules without the severe immune-related adverse events observed in patients receiving treatment with biologics (80). Indoleamine 2.3-dioxygenase (IDO1), an enzyme responsible for the oxidation of tryptophan into kynurenine, has been found overexpressed in many malignancies including melanoma. Blockade of IDO1 effectively restored IL-2 production resulting in direct reactivation of T cells in situ (73). Taking IDO1 as a novel therapeutic target for cancer immunotherapy, researchers have developed many highly potent and selective IDO1 inhibitors. Among them, epacadostat, an orally available pharmaceutical inhibitor of IDO1, exhibits potential immunomodulating and anti-neoplastic activities both in vitro and in vivo (89). Surprisingly, a closely-watched Phase III study combined anti-PD-1 antibody, Keytruda, with epacadostat for metastatic melanoma has failed given the lack of a significant improvement in progression-free survival, as well as the likely failure of the drug combination to extend overall survival.

Our study, for the first time, demonstrated that nNOS inhibitors effectively inhibited IFN-γ-inducible PD-L1 both in vitro and in vivo. These observations shed light to the use of pharmaceutical inhibitors targeting nNOS to rescue PD-L1-mediated immunosuppression in melanoma patients. Our study, in combination with accumulating evidence, indicates the important role of nNOS-mediated NO signaling in adaptive expression of PD-L1 upon exposure to IFN-γ, which provides a novel strategy for the development of efficient PD-L1 blockade therapies by targeting nNOS- NO signaling for human melanoma. Consistent with our in vitro observations, treatment with low-dose MAC-3-190 (5 mg/kg) effectively diminished the induction of tumor growth by IFN-γ. Of note, treatment with a newly synthesized nNOS inhibitor, HH044, alone also showed promising in vivo anti-melanoma activity.

Taken together, our study demonstrated that targeting nNOS-NO signaling using small molecular inhibitors may be an effective strategy for melanoma treatment given its novel mechanism of action; not only inhibiting nNOS-stimulated melanoma progression by reducing the production of NO, but also inhibiting IFN-γ-activated STAT1/3 and PD-L1. Armed with these highly selective, bio-available and potent inhibitors, our innovative approach targeting nNOS-NO will be of high impact when translated into a clinical setting within the next few years.

Innovation

Our study, for the first time, demonstrated the important role of nNOS in IFN-γ-stimulated melanoma progression both in vitro and in vivo, which sheds light on use of pharmaceutical inhibitors in targeting nNOS as an innovative approach to improve melanoma treatment. Our study also demonstrated the important role of nNOS in regulating IFN-γ-inducible PD-L1, which indicates that targeting nNOS may serve as a novel strategy of developing effective immunotherapy for melanoma patients using small synthetic molecules.

Materials and Methods

Cell lines, chemicals and reagents. The human melanoma cell lines A375, WM115, and Sk-mel-28 were obtained from American Type Culture Collection (ATCC; Manassas, VA), and WM3211 was obtained from Rockland Immunochemicals (Limerick, PA). Cell lines are cultured in Dulbecco's Modified Eagle's Medium (DMEM; #11995073; Gibco, Waltham, MA) (A375) or Eagle's Minimum Essential Medium (EMEM) (WM115, Sk-mel-28) with 10% fetal bovine serum (FBS; #26140079; Gibco, Waltham, MA), or Tumor Specialized Media with 2% FBS (WM3211). IFN-γ was purchased from Invitrogen (Thermo Fisher Scientific, Waltham, MA) and IFN-α was ordered from PBL Assay Science (Piscataway, NJ).

Antibodies. Mouse monoclonal anti-human NOS1, STAT3, p-STAT3, Lamin A/C (sc-17825; sc-8019; sc-8059; sc-398927; Santa Cruz Biotechnology, Dallas, TX) and mouse monoclonal anti-human β-Actin (8H10D10; Cell Signaling Technology, Danvers, MA) antibodies were used as primary antibodies; horseradish peroxidase-labeled anti-mouse (1:5,000; Cell Signaling Technology, Danvers, MA) was used as the secondary antibodies. Rabbit monoclonal PD-L1 conjugated with Alexa Fluor 488 (25048, Cell Signaling Technology, Danvers, MA) was used for extracellular expression analysis via flow cytometry and immunofluorescence.

Protein isolation and Western blotting. All samples were kept at 4° C. unless otherwise noted. Whole cell lysates were collected by incubating cell suspensions in 1× lysis buffer (9803S; Cell Signaling, Danvers, MA) with 1% protease inhibitor cocktail (PIC) for 15 minutes then lysed via sonication at 40% amplitude with 15 seconds on and 15 seconds off for 1 minute. Protein samples were isolated using centrifugation at 14,000 $g^{-1}$ for 10 minutes at 4° C.

Nuclear and cytosolic protein extraction is described elsewhere (84). Cells were collected via centrifugation and re-suspended in buffer A (10 mM HEPES, pH 7.9, 10 mM KCl, 0.150 mM $MgCl_2$, 0.5 mM DTT, 0.2 mM PMSF) with 1% PIC and allowed to swell for 10 minutes. 10% NP-40 was added and vortexed to lyse the cells. Samples were spun down at 14,000 $g^{-1}$ for 30 seconds to isolate the cytosolic fraction. The pelleted nuclei were re-suspended and incubated in buffer C (20 mM HEPES, 20% glycerol, 0.42 M NaCl, 0.15 mM $MgCl_2$, 0.2 mM EDTA, 0.5 mM DTT, and 0.2 mM PMSF) with 1% PIC then spun down at 14,000 $g^{-1}$ for 30 minutes to remove cell debris. Buffer D (20 mM HEPES, 20% glycerol, 50 mM KCl, 0.5 mM EDTA, 0.5 mM DTT, and 0.2 mM PMSF) was then added to dilute the nuclear sample.

Equal amounts of protein, as detected by Bradford assay, were loaded and resolved on 7.5% SDS-polyacrylamide gels, then transferred to Immobilon-$P^{SQ}$ polyvinylidene difluoride (PVDF) membranes (ISEQ00010; Merck KGaA, Darmstadt, Germany). The membranes were blocked using 10% non-fat milk (NOS1, STAT1/2, Actin, Lamin A/C) or 5% bovine serum albumin (BSA; SH3057402; Fisher Scientific, Waltham, MA) (p-STAT1/3), then incubated with primary antibodies for 1 hour at room temperature or overnight at 4° C., followed by secondary antibodies for 1 hour at room temperature as recommended by the manufacturer. Blots were washed extensively with TBS-T after each antibody incubation. Labeled bands were detected using SuperSignal horseradish peroxidase chemiluminescence reagents (1859674; 1859675; Thermo Fisher Scientific, Waltham, MA) and images were captured and analyzed using the Bio-Rad ChemiDoc $XRS^+$ System.

Reverse Phase Protein Array. Plated cells were treated with 250 units/mL of IFN-α or IFN-γ for 72 hours. After washing with 1×PBS, lysis buffer (1% Triton X-100, 50 mM HEPES, pH 7.4, 150 mM NaCl, 1.5 mM $MgCl_2$, 1 mM EGTA, 100 mM NaF, 10 mM Na pyrophosphate, 1 mM $Na_3VO_4$, 10% glycerol and 1% PIC) was added to the plates, followed by incubation on ice for 20 minutes with occasional shaking. Samples were then collected via scraping and spun down at 14,000 $g^{-1}$ for 10 minutes at 4° C. The protein concentration was then quantified by Bradford method and adjusted to 1.5 µg/µL with lysis buffer. Cell lysates were then mixed with 4×SDS sample buffer (40% glycerol, 8% SDS, 0.25M Tris-HCl, pH 6.8 with 10% BME). Miniscule amounts of serially diluted protein samples were then dotted on a nitrocellulose coated slide and probed with validated primary antibodies and a biotin-conjugated secondary antibody. The signals were amplified using Dako-Cytomation-Catalyzed system (Dako) and visualized by diaminobenzidine (DAB) colorimetric reaction. Dilution curves were fitted with Supercurve Fitting and the protein expressions normalized for protein loading.

Expression levels of PD-L1 detected by Flow Cytometry. Plated cells were treated with IFN-α or IFN-γ with or without 304 of nNOS inhibitors for 72 hours. Treated cells were collected via centrifugation and fixed using 4% formaldehyde in 1×PBS for 10 minutes at 37° C. The cells were then washed with incubation buffer (0.5% BSA in 1×PBS), followed by incubation with PD-L1 antibody in the dark for 2 hours at room temperature (1:100 dilution). Mean fluorescence intensities (MFI) were measured and recorded for analysis.

Expression levels of PD-L1 detected by Immunofluorescence. A375 cells were plated on coverslips and incubated with 250 units/mL of IFN-α or IFN-γ in the presence or absence of 304 of nNOS inhibitors for 72 hours. After treatment, cells on coverslips were fixed with 4% formaldehyde/PBS for 15 minutes at room temperature, followed by incubation with ice-cold 100% methanol for 10 minutes at −20° C. Samples were then incubated in blocking buffer (1×PBS, 5% horse serum, 0.3% Triton X-100) for 60 minutes, then in a 1:50 PD-L1 antibody dilution in dilution buffer (1×PBS, 1% BSA, 0.3% Triton X-100) overnight at 4° C. Stained specimens were rinsed with PBS then cured in the dark with DAPI fluorescence staining reagent for 1 hour. Slides were visualized and recorded using the BZ-X700 microscope (Keyence, Itasca, IL).

Detection of intracellular nitric oxide levels. Cultured cells in a 96-well plate were treated with 100 units/mL of IFN-α or IFN-γ for 48 hours. Once the incubation period was complete, the media was removed and replaced with Hank's Balanced Salt Solution (HBSS). 1 µM of 4-Amino-5-methylamino-2',7'-difluorofluorescein (DAF-FM) probe was added to each condition and fluorescence levels produced by DAF-FM were detected using a fluorescence microplate reader with excitation and emission wavelengths of 485 and 538 nm, respectively.

nNOS shRNA Knockdown. The knock down of nNOS was achieved using GIPZ lentiviral nNOS shRNAmir (Dharmacon, Lafayette, CO) with control shRNA. The shRNA was introduced into the cell using lipofectamine 2000 (Invitrogen, Carlsbad, CA). Stable cells carrying deficient nNOS were selected by puromycin incubation over 7 days and the knockdown of nNOS expression was confirmed by Western Blot.

In Vivo Xenograft Melanoma. All the animal procedures were approved by the Institutional Animal Care and Use Committee (IACUC) at Chapman University. Nude mice (Nu/Nu) were purchased from Charles River (Wilmington, MA) and were housed and maintained in the Chapman University vivarium under pathogen-free conditions. Human A375 metastatic melanoma cells were suspended in cold Matrigel (354248; Corning, Corning, NY) and injected subcutaneously into the flank of the mouse ($1 \times 10^6$ cells per mouse) to establish tumors. The mice were treated with intraperitoneal injections of normal saline or IFN-γ (1000 units/mouse) with or without MAC-3-190 (5 mg/kg/day) for 21 days. The growth of the tumors was monitored three times a week and measured using digital Vernier calipers. Tumor growth was calculated as tumor volume (mm$^3$)= [Length×(Width$^2$)]/2. The mice were sacrificed after 21 days and tumor xenografts and lungs were removed and weighed. Half of the tumor xenograft was fixed in a 10% formalin solution and the other half was processed for flow cytometry. The fixed samples were then further embedded in paraffin wax for sectioning and stained with specific antibodies using the Ventana Benchmark Ultra machine to visualize the expression of PD-L1 (790-4905; Ventana, Oro Valley, AZ) and CD8$^+$ T cells (108M-98; Cell Marque, Rocklin, CA). The percentage of PD-L1 stained positive cells were counted using ImageJ (https://imagej.nih.gov/ij/index.html). Xenograft tumor samples for flow cytometry were dissociated into a single cell suspension using the gentleMACS Dissociator from Miltenyi Biotec (130-095-929; Auburn, CA) following the standard protocol for soft tumors. Single cell suspensions were then fixed and stained with PD-L1 antibodies as described above.

Statistical Analyses. All the experiments were performed in at least two different human melanoma cell lines. Data shown are means±SD from a representative of at least two independent experiments. Statistical analysis was performed by using the Student t-test and a p value of less than 0.05 was considered statistically significant.

Abbreviations

| | |
|---|---|
| APC | Antigen presenting cells |
| APE/Ref-1 | Apurinic (apyrimidinic) endonuclease/redox-factor-1 |
| BRAF | B-raf proto-oncogene |
| BSA | Bovine serum albumin |
| c-MYC | MYC proto-oncogene |
| CM | Cutaneous melanoma |
| CNS | Central nervous system |
| CTL | Cytotoxic lymphocyte |
| DAF-FM | 4-Amino-5-methylamino-2',7'-difluorofluorescein |
| DAPI | 4',6-diamidino-2-phenylindole |
| DMEM | Dulbecco's Modified Eagle's Medium |
| DNA | Deoxyribonucleic acid |
| EMEM | Eagle's Minimum Essential Medium |
| eNOS | Endothelial nitric oxide synthase |
| FBS | Fetal bovine serum |
| Foxp3 | Forkhead box P3 |
| GAS | Gamma activated sequence |
| HBSS | Hank's Balanced Salt Solution |
| HGF/SF | Hepatocyte growth factor/scatter factor |
| HIF1α | Hypoxia-inducible factor 1-alpha |
| IACUC | Institutional Animal Care and Use Committee |
| IC50 | Half maximal inhibitory concentration |
| IDO-1 | Indoleamine 2,3-dioxygenase 1 |
| IFN-α | Interferon-alpha |
| IFN-γ | Interferon-gamma |
| IL | Interleukins |
| iNOS | Inducible nitric oxide synthase |
| IRF | Interferon regulatory factor |
| JAK | Janus kinase |
| mAb | Monoclonal antibody |
| MFI | Mean fluorescence intensity |
| NF-κB | Nuclear factor kappa-light-chain-enhancer of activated B cells |
| NK | Natural killer cells |
| NKT | Natural killer T cells |
| nNOS | Neuronal nitric oxide synthase |
| NO | Nitric oxide |
| 8-oxo-dG | 8-oxo-7,8-dihydro-2 -deoxyguanosine |
| p53 | Tumor suppressor p53 gene |
| PBS | Phosphate buffered saline |
| PD-1 | Programmed death receptor-1 |
| PD-L1 | Programmed death-ligand 1 |
| PFS | Progression free survival |
| PI3K/AKT | Phosphoinositide 3-kinase/protein kinase B |
| PIC | Protease inhibitor cocktail |
| pSTAT | Phosphorylated signal transducer and activator of transcription |
| PVDF | Polyvinylidene difluoride |
| RNS | Reactive nitrogen species |
| ROS | Reactive oxygen species |
| RPPA | Reverse phase protein array |
| shRNA | Short hairpin ribonucleic acid |
| STAT | Signal transducer and activator of transcription |
| SWOG | Southwest Oncology Group |
| TBS-T | Tris buffered saline-Tween |
| TCR | T cell receptor |
| Th1/2 | T helper 1/2 cells |
| TIL | Tumor infdtrating lymphocyte |
| TME | Tumor microenvironment |
| Treg | Regulatory T cells |
| UVR | Ultraviolet radiation |

REFERENCES 1. 2017. Key Statistics for Melanoma Skin Cancer American Cancer Society. https://www.cancer.org/cancer/melanoma-skin-cancer/about/key-statistics.html 2017 Apr. 17.
2. Achkar T, Tarhini A A. The use of immunotherapy in the treatment of melanoma. J Hematol Oncol 10: 88, 2017.
3. Ahmed B, Van Den Oord J J. Expression of the neuronal isoform of nitric oxide synthase (nNOS) and its inhibitor, protein inhibitor of nNOS, in pigment cell lesions of the skin. Br J Dermatol 141: 12-9, 1999.

4. Albina J E, Abate J A, Henry W L. Nitric-Oxide Production Is Required for Murine Resident Peritoneal-Macrophages to Suppress Mitogen-Stimulated T-Cell Proliferation—Role of Ifn-Gamma in the Induction of the Nitric Oxide-Synthesizing Pathway. Journal of Immunology 147: 144-148, 1991.
5. Albina J E, Abate J A, Henry W L, Jr. Nitric oxide production is required for murine resident peritoneal macrophages to suppress mitogen-stimulated T cell proliferation. Role of IFN-gamma in the induction of the nitric oxide-synthesizing pathway. J Immunol 147: 144-8, 1991.
6. Almuriekhi M, Shintani T, Fahiminiya S, Fujikawa A, Kuboyama K, Takeuchi Y, Nawaz Z, Nadaf J, Kamel H, Kitam A K, Samiha Z, Mahmoud L, Ben-Omran T, Majewski J, Noda M. Loss-of-Function Mutation in APC2 Causes Sotos Syndrome Features. Cell Rep, 2015.
7. Audrito V, Serra S, Stingi A, Orso F, Gaudino F, Bologna C, Neri F, Garaffo G, Nassini R, Baroni G, Rulli E, Massi D, Oliviero S, Piva R, Taverna D, Mandala M, Deaglio S. PD-L1 up-regulation in melanoma increases disease aggressiveness and is mediated through miR-17-5p. Oncotarget 8: 15894-15911, 2017.
8. Avalle L, Pensa S, Regis G, Novelli F, Poli V. STAT1 and STAT3 in tumorigenesis: A matter of balance. JAKSTAT 1: 65-72, 2012.
9. Bald T, Landsberg J, Lopez-Ramos D, Renn M, Glodde N, Jansen P, Gaffal E, Steitz J, Tolba R, Kalinke U, Limmer A, Jonsson G, Holzel M, Tuting T. Immune cell-poor melanomas benefit from PD-1 blockade after targeted type I IFN activation. Cancer Discov 4: 674-87, 2014.
10. Bauer J, Buttner P, Murali R, Okamoto I, Kolaitis N A, Landi M T, Scolyer R A, Bastian B C. BRAF mutations in cutaneous melanoma are independently associated with age, anatomic site of the primary tumor, and the degree of solar elastosis at the primary tumor site. Pigment Cell Melanoma Res 24: 345-51, 2011.
11. Bhat P, Leggatt G, Waterhouse N, Frazer I H. Interferon-gamma derived from cytotoxic lymphocytes directly enhances their motility and cytotoxicity. Cell Death Dis 8: e2836, 2017.
12. Buettner R, Mora L B, Jove R. Activated STAT signaling in human tumors provides novel molecular targets for therapeutic intervention. Clin Cancer Res 8: 945-54, 2002.
13. Byrne E H, Fisher D E. Immune and molecular correlates in melanoma treated with immune checkpoint blockade. Cancer 123: 2143-2153, 2017.
14. Cardoso A A, Jiang Y, Luo M, Reed A M, Shanda S, He Y, Maitra A, Kelley M R, Fishel M L. APE1/Ref-1 regulates STAT3 transcriptional activity and APE1/Ref-1-STAT3 dual-targeting effectively inhibits pancreatic cancer cell survival. PLoS One 7: e47462, 2012.
15. Chen Y, Zhang Z, Luo C, Chen Z, Zhou J. MicroRNA-18b inhibits the growth of malignant melanoma via inhibition of HIF-1alpha-mediated glycolysis. Oncol Rep 36: 471-9, 2016.
16. Cheng L, Lopez-Beltran A, Massari F, MacLennan G T, Montironi R. Molecular testing for BRAF mutations to inform melanoma treatment decisions: a move toward precision medicine. Mod Pathol 31: 24-38, 2018.
17. Cinelli M A, Li H, Chreifi G, Poulos T L, Silverman R B. Nitrile in the Hole: Discovery of a Small Auxiliary Pocket in Neuronal Nitric Oxide Synthase Leading to the Development of Potent and Selective 2-Aminoquinoline Inhibitors. J Med Chem 60: 3958-3978, 2017.
18. Cinelli M A, Li H, Pensa A V, Kang S, Roman L J, Martasek P, Poulos T L, Silverman R B. Phenyl Ether- and Aniline-Containing 2-Aminoquinolines as Potent and Selective Inhibitors of Neuronal Nitric Oxide Synthase. J Med Chem 58: 8694-712, 2015.
19. Concha-Benavente F, Srivastava R M, Trivedi S, Lei Y, Chandran U, Seethala R R, Freeman G J, Ferris R L. Identification of the Cell-Intrinsic and -Extrinsic Pathways Downstream of EGFR and IFNgamma That Induce PD-L1 Expression in Head and Neck Cancer. Cancer Res 76: 1031-43, 2016.
20. Creagan E T, Ahmann D L, Long H J, Frytak S, Sherwin S A, Chang M N. Phase II study of recombinant interferon-gamma in patients with disseminated malignant melanoma. Cancer Treat Rep 71: 843-4, 1987.
21. Domingues B, Lopes J M, Soares P, Populo H. Melanoma treatment in review. Immunotargets Ther 7: 35-49, 2018.
22. Dupin E, Le Douarin N M. Development of melanocyte precursors from the vertebrate neural crest. Oncogene 22: 3016-23, 2003.
23. Ernstoff M S, Trautman T, Davis C A, Reich S D, Witman P, Balser J, Rudnick S, Kirkwood J M. A randomized phase I/II study of continuous versus intermittent intravenous interferon gamma in patients with metastatic melanoma. J Clin Oncol 5: 1804-10, 1987.
24. Ferrantini M, Giovarelli M, Modesti A, Musiani P, Modica A, Venditti M, Peretti E, Lollini P L, Nanni P, Forni G, et al. IFN-alpha 1 gene expression into a metastatic murine adenocarcinoma (TS/A) results in CD8+ T cell-mediated tumor rejection and development of antitumor immunity. Comparative studies with IFN-gamma-producing TS/A cells. J Immunol 153: 4604-15, 1994.
25. Ferrer P, Asensi M, Priego S, Benlloch M, Mena S, Ortega A, Obrador E, Esteve J M, Estrela J M. Nitric oxide mediates natural polyphenol-induced Bcl-2 down-regulation and activation of cell death in metastatic B16 melanoma. J Biol Chem 282: 2880-90, 2007.
26. Fotiou S, Fotiou D, Deliconstantinos G. Formation of heme-iron complexes with nitric oxide (NO) and peroxynitrite (ONOO—) after ultraviolet radiation as a protective mechanism in rat skin. In Vivo 23: 281-6, 2009
27. Garbe C, Eigentler T K, Keilholz U, Hauschild A, Kirkwood J M. Systematic Review of Medical Treatment in Melanoma: Current Status and Future Prospects. The Oncologist 16: 5-24, 2011.
28. Garcia-Diaz A, Shin D S, Moreno B H, Saco J, Escuin-Ordinas H, Rodriguez G A, Zaretsky J M, Sun L, Hugo W, Wang X, Parisi G, Saus C P, Torrejon D Y, Graeber T G, Comin-Anduix B, Hu-Lieskovan S, Damoiseaux R, Lo R S, Ribas A. Interferon Receptor Signaling Pathways Regulating PD-L1 and PD-L2 Expression. Cell Rep 19: 1189-1201, 2017.
29. Gowrishankar K, Gunatilake D, Gallagher S J, Tiffen J, Rizos H, Hersey P. Inducible but not constitutive expression of PD-L1 in human melanoma cells is dependent on activation of NF-kappaB. PLoS One 10: e0123410, 2015.
30. Gowrishankar K, Gunatilake D, Gallagher S J, Tiffen J, Rizos H, Hersey P. Inducible but Not Constitutive Expression of PD-L1 in Human Melanoma Cells Is Dependent on Activation of NF-?B. In: PLoS One. edited by Cheriyath V. San Francisco, CA. USA; 2015.
31. Halliday G M. Inflammation, gene mutation and photo-immunosuppression in response to UVR-induced oxidative damage contributes to photocarcinogenesis. Mutat Res 571: 107-20, 2005.

32. Halliday G M, Byrne S N, Kuchel J M, Poon T S, Barnetson R S. The suppression of immunity by ultraviolet radiation: UVA, nitric oxide and DNA damage. Photochem Photobiol Sci 3: 736-40, 2004.
33. Hanna S C, Krishnan B, Bailey S T, Moschos S J, Kuan P F, Shimamura T, Osborne L D, Siegel M B, Duncan L M, O'Brien E T, Superfine R, Miller C R, Simon M C, Wong K K, Kim W Y. HIF1 alpha and HIF2 alpha independently activate SRC to promote melanoma metastases. Journal of Clinical Investigation 123: 2078-2093, 2013.
34. Holly E A, Aston D A, Cress R D, Ahn D K, Kristiansen J J. Cutaneous melanoma in women. I. Exposure to sunlight, ability to tan, and other risk factors related to ultraviolet light. Am J Epidemiol 141: 923-33, 1995.
35. Jaiswal M, LaRusso N F, Burgart L J, Gores G J. Inflammatory cytokines induce DNA damage and inhibit DNA repair in cholangiocarcinoma cells by a nitric oxide-dependent mechanism. Cancer Res 60: 184-90, 2000.
36. Joshi M, Strandhoy J, White W L. Nitric oxide synthase activity is up-regulated in melanoma cell lines: a potential mechanism for metastases formation. Melanoma Res 6: 121-6, 1996.
37. Juneja V R, McGuire K A, Manguso R T, LaFleur M W, Collins N, Haining W N, Freeman G J, Sharpe A H. PD-L1 on tumor cells is sufficient for immune evasion in immunogenic tumors and inhibits CD8 T cell cytotoxicity. J Exp Med, 2017.
38. Kakuta S, Tagawa Y, Shibata S, Nanno M, Iwakura Y. Inhibition of B16 melanoma experimental metastasis by interferon-gamma through direct inhibition of cell proliferation and activation of antitumour host mechanisms. Immunology 105: 92-100, 2002.
39. Kaunitz G J, Cottrell T R, Lilo M, Muthappan V, Esandrio J, Berry S, Xu H, Ogurtsova A, Anders R A, Fischer A H, Kraft S, Gerstenblith M R, Thompson C L, Honda K, Cuda J D, Eberhart C G, Handa J T, Lipson E J, Taube J M. Melanoma subtypes demonstrate distinct PD-L1 expression profiles. Lab Invest 97: 1063-1071, 2017.
40. Kortylewski M, Jove R, Yu H. Targeting STAT3 affects melanoma on multiple fronts. Cancer Metastasis Rev 24: 315-27, 2005.
41. Kraehn G M, Utikal J, Udart M, Greulich K M, Bezold G, Kaskel P, Leiter U, Peter R U. Extra c-myc oncogene copies in high risk cutaneous malignant melanoma and melanoma metastases. Br J Cancer 84: 72-9, 2001.
42. Kugel C H, 3rd, Douglass S M, Webster M R, Kaur A, Liu Q, Yin X, Weiss S A, Darvishian F, Al-Rohil R N, Ndoye A, Behera R, Alicea G M, Ecker B L, Fane M, Allegrezza M J, Svoronos N, Kumar V, Wang D Y, Somasundaram R, Hu-Lieskovan S, Ozgun A, Herlyn M, Conejo-Garcia J R, Gabrilovich D, Stone E L, Nowicki T S, Sosman J, Rai R, Carlino M S, Long G V, Marais R, Ribas A, Eroglu Z, Davies M A, Schilling B, Schadendorf D, Xu W, Amaravadi R K, Menzies A M, McQuade J L, Johnson D B, Osman I, Weeraratna A T. Age Correlates with Response to Anti-PD1, Reflecting Age-Related Differences in Intratumoral Effector and Regulatory T-Cell Populations. Clin Cancer Res, 2018.
43. Lawrence M S, Stojanov P, Polak P, Kryukov G V, Cibulskis K, Sivachenko A, Carter S L, Stewart C, Mermel C H, Roberts S A, Kiezun A, Hammerman P S, McKenna A, Drier Y, Zou L, Ramos A H, Pugh T J, Stransky N, Helman E, Kim J, Sougnez C, Ambrogio L, Nickerson E, Shefler E, Cortes M L, Auclair D, Saksena G, Voet D, Noble M, DiCara D, Lin P, Lichtenstein L, Heiman D I, Fennell T, Imielinski M, Hernandez B, Hodis E, Baca S, Dulak A M, Lohr J, Landau D A, Wu C J, Melendez-Zajgla J, Hidalgo-Miranda A, Koren A, McCarroll S A, Mora J, Crompton B, Onofrio R, Parkin M, Winckler W, Ardlie K, Gabriel S B, Roberts C W M, Biegel J A, Stegmaier K, Bass A J, Garraway L A, Meyerson M, Golub T R, Gordenin D A, Sunyaev S, Lander E S, Getz G. Mutational heterogeneity in cancer and the search for new cancer-associated genes. Nature 499: 214-218, 2013.
44. Lee I C, Huang Y H, Chau G Y, Huo T I, Su C W, Wu J C, Lin H C. Serum interferon gamma level predicts recurrence in hepatocellular carcinoma patients after curative treatments. Int J Cancer 133: 2895-902, 2013.
45. Lin X, Sun R, Zhao X L, Zhu D W, Zhao X M, Gu Q, Dong X Y, Zhang D F, Zhang Y H, Li Y L, Sun B C. C-myc overexpression drives melanoma metastasis by promoting vasculogenic mimicry via c-myc/snail/Bax signaling. Journal of Molecular Medicine-Jmm 95: 53-67, 2017.
46. Liu Q, Tomei S, Ascierto M L, De Giorgi V, Bedognetti D, Dai C, Uccellini L, Spivey T, Pos Z, Thomas J, Reinboth J, Murtas D, Zhang Q, Chouchane L, Weiss G R, Slingluff C L, Jr., Lee P P, Rosenberg S A, Alter H, Yao K, Wang E, Marincola F M. Melanoma NOS1 expression promotes dysfunctional IFN signaling. J Clin Invest 124: 2147-59, 2014.
47. Livden J K, Bjerke J R, Degre M, Matre R. Effect of UV radiation on interferon, immunoglobulins and complement components in serum from healthy individuals. Photodermatol 4: 296-301, 1987.
48. Loftus S K, Baxter L L, Cronin J C, Fufa T D, Program N C S, Pavan W J. Hypoxia-induced HIF1alpha targets in melanocytes reveal a molecular profile associated with poor melanoma prognosis. Pigment Cell Melanoma Res 30: 339-352, 2017.
49. Lollini P L, De Giovanni C, Nicoletti G, Bontadini A, Tazzari P L, Landuzzi L, Scotlandi K, Nanni P. Enhancement of experimental metastatic ability by tumor necrosis factor-alpha alone or in combination with interferon-gamma. Clin Exp Metastasis 8: 215-24, 1990.
50. Lollini P L, Nanni P, de Giovanni C, Nicoletti G, Landuzzi L. Re: Randomized trial of adjuvant human interferon gamma versus observation in high-risk cutaneous melanoma: a Southwest Oncology Group study. J Natl Cancer Inst 88: 926-7, 1996.
51. Lorenz P, Roychowdhury S, Engelmann M, Wolf G, Horn T F. Oxyresveratrol and resveratrol are potent antioxidants and free radical scavengers: effect on nitrosative and oxidative stress derived from microglial cells. Nitric Oxide 9: 64-76, 2003.
52. MacMicking J, Xie Q W, Nathan C. Nitric oxide and macrophage function. Annu Rev Immunol 15: 323-50, 1997.
53. Maldonado J L, Fridlyand J, Patel H, Jain A N, Busam K, Kageshita T, Ono T, Albertson D G, Pinkel D, Bastian B C. Determinants of BRAF mutations in primary melanomas. J Natl Cancer Inst 95: 1878-90, 2003.
54. Marzec M, Zhang Q, Goradia A, Raghunath P N, Liu X, Paessler M, Wang H Y, Wysocka M, Cheng M, Ruggeri B A, Wasik M A. Oncogenic kinase NPM/ALK induces through STAT3 expression of immunosuppressive protein CD274 (PD-L1, B7-H1). Proc Natl Acad Sci USA 105: 20852-7, 2008.
55. Mauldin I S, Wages N A, Stowman A M, Wang E, Smolkin M E, Olson W C, Deacon D H, Smith K T, Galeassi N V, Chianese-Bullock K A, Dengel L T, Marincola F M, Petroni G R, Mullins D W, Slingluff C L, Jr. Intratumoral interferon-gamma increases chemokine production but fails to increase T cell infiltration of human melanoma metastases. Cancer Immunol Immunother 65: 1189-99, 2016.
56. McGary E C, Lev D C, Bar-Eli M. Cellular adhesion pathways and metastatic potential of human melanoma. Cancer Biol Ther 1: 459-65, 2002.
57. Meissl K, Macho-Maschler S, Muller M, Strobl B. The good and the bad faces of STAT1 in solid tumours. Cytokine 89: 12-20, 2017.
58. Meyskens F L, Jr., Kopecky K, Samson M, Hersh E, Macdonald J, Jaffe H, Crowley J, Coltman C. Recombinant human interferon gamma: adverse effects in high-risk stage I and II cutaneous malignant melanoma. J Natl Cancer Inst 82: 1071, 1990.
59. Meyskens F L, Jr., Kopecky K J, Taylor C W, Noyes R D, Tuthill R J, Hersh E M, Feun L G, Doroshow J H, Flaherty L E, Sondak V K. Randomized trial of adjuvant human interferon gamma versus observation in high-risk cutaneous melanoma: a Southwest Oncology Group study. J Natl Cancer Inst 87: 1710-3, 1995.
60. Mimura K, Teh J L, Okayama H, Shiraishi K, Kua L F, Koh V, Smoot D T, Ashktorab H, Oike T, Suzuki Y, Fazreen Z, Asuncion B R, Shabbir A, Yong W P, So J, Soong R, Kono K. PD-L1 expression is mainly regulated by interferon gamma associated with JAK-STAT pathway in gastric cancer. Cancer Sci 109: 43-53, 2018.
61. Moscow J A, Fojo T, Schilsky R L. The evidence framework for precision cancer medicine. Nat Rev Clin Oncol 15: 183-192, 2018.
62. Noonan F P, Dudek J, Merlino G, De Fabo E C. Animal models of melanoma: an HGF/SF transgenic mouse model may facilitate experimental access to UV initiating events. Pigment Cell Res 16: 16-25, 2003.
63. Osterlind A, Tucker M A, Stone B J, Jensen O M. The Danish case-control study of cutaneous malignant melanoma. II. Importance of UV-light exposure. Int J Cancer 42: 319-24, 1988.
64. Pensa A V, Cinelli M A, Li H, Chreifi G, Mukherjee P, Roman L J, Martasek P, Poulos T L, Silverman R B. Hydrophilic, Potent, and Selective 7-Substituted 2-Aminoquinolines as Improved Human Neuronal Nitric Oxide Synthase Inhibitors. J Med Chem 60: 7146-7165, 2017.
65. Ponsonby A L, McMichael A, van der Mei I. Ultraviolet radiation and autoimmune disease: insights from epidemiological research. Toxicology 181-182: 71-8, 2002.
66. Prasad R, Katiyar S K. Crosstalk Among UV-Induced Inflammatory Mediators, DNA Damage and Epigenetic Regulators Facilitates Suppression of the Immune System. Photochem Photobiol, 2016.
67. Ray S, Lee C, Hou T, Bhakat K K, Brasier A R. Regulation of signal transducer and activator of transcription 3 enhanceosome formation by apurinic/apyrimidinic endonuclease 1 in hepatic acute phase response. Mol Endocrinol 24: 391-401, 2010.
68. Schoenborn J R, Wilson C B. Regulation of interferon-gamma during innate and adaptive immune responses. Adv Immunol 96: 41-101, 2007.
69. Schultz J, Koczan D, Schmitz U, Ibrahim S M, Pilch D, Landsberg J, Kunz M. Tumor-promoting role of signal transducer and activator of transcription (Stat)1 in late-stage melanoma growth. Clin Exp Metastasis 27: 133-40, 2010.
70. Shen J, Bao S, Reeve V E. Modulation of IL-10, IL-12, and IFN-gamma in the epidermis of hairless mice by UVA (320-400 nm) and UVB (280-320 nm) radiation. J Invest Dermatol 113: 1059-64, 1999.
71. Simon S, Labarriere N. PD-1 expression on tumor-specific T cells: Friend or foe for immunotherapy? Oncoimmunology 7: e1364828, 2017.
72. Simons D L, Lee G, Kirkwood J M, Lee P P. Interferon signaling patterns in peripheral blood lymphocytes may predict clinical outcome after high-dose interferon therapy in melanoma patients. J Transl Med 9: 52, 2011.
73. Spranger S, Koblish H K, Horton B, Scherle P A, Newton R, Gajewski T F. Mechanism of tumor rejection with doublets of CTLA-4, PD-1/PD-L1, or IDO blockade involves restored IL-2 production and proliferation of CD8(+) T cells directly within the tumor microenvironment. J Immunother Cancer 2: 3, 2014.
74. Tanese K, Hashimoto Y, Berkova Z, Wang Y, Samaniego F, Lee J E, Ekmekcioglu S, Grimm E A. Cell Surface CD74-MIF Interactions Drive Melanoma Survival in Response to Interferon-gamma. J Invest Dermatol 135: 2775-84, 2015.
75. Tang C H, Grimm E A. Depletion of endogenous nitric oxide enhances cisplatin-induced apoptosis in a p53-dependent manner in melanoma cell lines. J Biol Chem 279: 288-98, 2004.
76. Taube J M, Anders R A, Young G D, Xu H, Sharma R, McMiller T L, Chen S, Klein A P, Pardoll D M, Topalian S L, Chen L. Colocalization of inflammatory response with B7-h1 expression in human melanocytic lesions supports an adaptive resistance mechanism of immune escape. Sci Transl Med 4: 127ra37, 2012.
77. Teixeira L K, Fonseca B P, Barboza B A, Viola J P. The role of interferon-gamma on immune and allergic responses. Mem Inst Oswaldo Cruz 100 Suppl 1: 137-44, 2005.
78. Tumeh P C, Harview C L, Yearley J H, Shintaku I P, Taylor E J, Robert L, Chmielowski B, Spasic M, Henry G, Ciobanu V, West A N, Carmona M, Kivork C, Seja E, Cherry G, Gutierrez A J, Grogan T R, Mateus C, Tomasic G, Glaspy J A, Emerson R O, Robins H, Pierce R H, Elashoff D A, Robert C, Ribas A. PD-1 blockade induces responses by inhibiting adaptive immune resistance. Nature 515: 568-71, 2014.
79. Vannini F, Kashfi K, Nath N. The dual role of iNOS in cancer. Redox Biol 6: 334-43, 2015.
80. Weinmann H. Cancer Immunotherapy: Selected Targets and Small-Molecule Modulators. ChemMedChem 11: 450-66, 2016.
81. Yamazaki T, Akiba H, Koyanagi A, Azuma M, Yagita H, Okumura K. Blockade of B7-H1 on macrophages suppresses CD4+ T cell proliferation by augmenting IFN-gamma-induced nitric oxide production. J Immunol 175: 1586-92, 2005.
82. Yang S, Irani K, Heffron S E, Jurnak F, Meyskens F L, Jr. Alterations in the expression of the apurinic/apyrimidinic endonuclease-1/redox factor-1 (APE/Ref-1) in human melanoma and identification of the therapeutic potential of resveratrol as an APE/Ref-1 inhibitor. Mol Cancer Ther 4: 1923-35, 2005.
83. Yang S, Meyskens F L. Apurinic/apyrimidinic endonuclease/redox effector factor-1 (APE/Ref-1): a unique target for the prevention and treatment of human melanoma. Antioxid Redox Signal 11: 639-50, 2009.
84. Yang S, Meyskens F L, Jr. Alterations in activating protein 1 composition correlate with phenotypic differentiation changes induced by resveratrol in human melanoma. Mol Pharmacol 67: 298-308, 2005.

85. Yang Z, Misner B, Ji H, Poulos T L, Silverman R B, Meyskens F L, Yang S. Targeting nitric oxide signaling with nNOS inhibitors as a novel strategy for the therapy and prevention of human melanoma. Antioxid Redox Signal 19: 433-47, 2013.
86. Yang Z, Misner B, Ji H, Poulos T L, Silverman R B, Meyskens F L, Yang S. Targeting Nitric Oxide Signaling with nNOS Inhibitors As a Novel Strategy for the Therapy and Prevention of Human Melanoma. Antioxid Redox Signal, 2013.
87. Yang Z, Yang S, Misner B J, Chiu R, Liu F, Meyskens F L, Jr. Nitric oxide initiates progression of human melanoma via a feedback loop mediated by apurinic/apyrimidinic endonuclease-1/redox factor-1, which is inhibited by resveratrol. Mol Cancer Ther 7: 3751-60, 2008.
88. Yazdi A S, Palmedo G, Flaig M J, Puchta U, Reckwerth A, Rutten A, Mentzel T, Hugel H, Hantschke M, Schmid-Wendtner M H, Kutzner H, Sander C A. Mutations of the BRAF gene in benign and malignant melanocytic lesions. J Invest Dermatol 121: 1160-2, 2003.
89. Yue E W, Sparks R, Polam P, Modi D, Douty B, Wayland B, Glass B, Takvorian A, Glenn J, Zhu W, Bower M, Liu X, Leffet L, Wang Q, Bowman K J, Hansbury M J, Wei M, Li Y, Wynn R, Burn T C, Koblish H K, Fridman J S, Emm T, Scherle P A, Metcalf B, Combs A P. INCB24360 (Epacadostat), a Highly Potent and Selective Indoleamine-2,3-dioxygenase 1 (IDO1) Inhibitor for Immuno-oncology. ACS Med Chem Lett 8: 486-491, 2017.
90. Zaidi M R, Davis S, Noonan F P, Graff-Cherry C, Hawley T S, Walker R L, Feigenbaum L, Fuchs E, Lyakh L, Young H A, Hornyak T J, Arnheiter H, Trinchieri G, Meltzer P S, De Fabo E C, Merlino G. Interferon-gamma links ultraviolet radiation to melanomagenesis in mice. Nature 469: 548-53, 2011.
91. Zaidi M R, Davis S, Noonan F P, Graff-Cherry C, Hawley T S, Walker R L, Feigenbaum L, Fuchs E, Lyakh L, Young H A, Hornyak T J, Arnheiter H, Trinchieri G, Meltzer P S, De Fabo E C, Merlino G. Interferon-? links UV to melanocyte activation and promotes melanoma-genesis. Nature 469: 548-53, 2011.
92. Zaidi M R, De Fabo E C, Noonan F P, Merlino G. Shedding light on melanocyte pathobiology in vivo. Cancer Res 72: 1591-5, 2012.
93. Zaretsky J M, Garcia-Diaz A, Shin D S, Escuin-Ordinas H, Hugo W, Hu-Lieskovan S, Torrejon D Y, Abril-Rodriguez G, Sandoval S, Barthly L, Saco J, Homet Moreno B, Mezzadra R, Chmielowski B, Ruchalski K, Shintaku I P, Sanchez P J, Puig-Saus C, Cherry G, Seja E, Kong X, Pang J, Berent-Maoz B, Comin-Anduix B, Graeber T G, Tumeh P C, Schumacher T N, Lo R S, Ribas A. Mutations Associated with Acquired Resistance to PD-1 Blockade in Melanoma. N Engl J Med 375: 819-29, 2016.
94. Zitvogel L, Kroemer G. Targeting PD-1/PD-L1 interactions for cancer immunotherapy. Oncoimmunology 1: 1223-1225, 2012.

Example 2—HH044: Anti-Melanoma Activity and In Vivo Drug Biodistribution Detection and Imaging Methods In Vivo Anti-Melanoma Activity of HH044

1) Tumor growth and HH044 treatment: Female athymic nude mice (4-6 weeks old, Nu/Nu 088 Homozygous) were purchased from Charles River (Wilmington, MA). The animal studies were conducted with approval from the Institutional Animal Care and Use Committee (IACUC) of Chapman University (Irvine, CA). The mice were injected subcutaneously with $1 \times 10^6$ A375 human melanoma cells in 200 µL solution of 50% Matrigel basement membrane matrix (CB354248, Corning, Corning, NY). Three days later, mice were randomly allocated to different experimental treatment groups. nNOS inhibitor HH044 was injected intraperitoneally once daily for 21 days (20 mg/kg) in comparison to vehicle-treated controls. The body weights and tumor sizes were measured twice weekly until the end of the study.

2) PD-L1 expression levels in A375 melanoma xenografts: By the end of the study, a portion of the xenograft tumor samples was processed for flow cytometry via dissociation into a single cell suspension using the GentleMACS Dissociator from Miltenyi Biotec (130-095-929; Auburn, CA) following the standard protocol for soft tumors. Single cell suspensions were then collected and fixed using 4% formaldehyde in 1×PBS for 10 min at 37° C. The cells were then washed with incubation buffer (0.5% BSA in 1×PBS), followed by incubation with PD-L1 antibody in the dark for 2 h at room temperature (1:100 dilution). Mean fluorescence intensities (MFI) were measured and recorded for analysis.

In Vivo Biodistribution Detection

1) Isolation of compound from tissue samples: Saline or HH044 in a dose of 20 mg/kg/day was administered via intraperitoneal injections (n=6 for each group) for 4 weeks. Tumors and organs were then collected and weighed. 300 µL of Milli-Q water was added to every 100 mg of tissue followed by manual homogenization. Homogenates were then mixed with an equal volume of acetonitrile by vortexing before centrifuging at 2500 $g^{-1}$ for 4 min at 4° C. 1 mL of Milli-Q water was added to the collected supernatant then 6 mL of a mixture of chloroform and isopropanol (1:1 ratio) for extraction. The mixture was mixed via vortex and centrifuged at 2500 $g^{-1}$ for 5 min at 4° C. The collected organic layer was further concentrated using a Speedvac to evaporate the solvent. Dried samples were redissolved in methanol and the presence of the compound was determined using MALDI-TOF.

2) Liquid Chromatography-Mass Spectrometry (LC-MS): Samples containing HH044, as determined by MALDI-TOF, were further analyzed via LC-MS. An internal standard with a known concentration of 1 µM was used to determine the concentration of HH044. Chromatography separation was performed on a Shimadzu Premier C18 column (3.0 µm, 4.6×100 mm) using a Shimadzu HPLC-MS 2020 system (Shimadzu MS Technologies, Japan). 20 µL of each sample was eluted at a flow rate of 0.4 mL/min, using a mobile phase consisting of 0.05% formic acid in water and acetonitrile. The proportion of acetonitrile in the mobile phase was optimized as follows: 0-3 min, 15%; 3-15 min, 55%; 15-18 min, 100%; 18-23 min 5%. Mass spectrometry was carried out on a Shimadzu 2020 mass spectrometer with an ESI interface operating in positive ion mode. Determined concentrations of HH044 in tissues were normalized to the weight of the sample [1].

Figure 10:
FIG. 10. In vivo distribution of HH044 in melanoma xenograft mouse model. A) HH044 was conjugated with VivoTag 680XL via a beta-alanine linker for in vivo imaging and tracking. B) Ex vivo and C) in vivo imaging of compound distribution after administration of HH044-VivoTag conjugates at different time points as detected by IVIS Imaging system (PerkinElmer®). (D and E) HH044 detected from tumor xenografts 24 h after administration using Liquid Chromatography-Mass Spectrometry (LCMS) (D) and using matrix-assisted laser desorption/ionization time-of-flight (MALDI-TOF) mass spectrometry (E). Drug samples were prepared as described before [2]. Tumor tissues were homogenized and a mixture of chloroform and isopropanol (1:1 ratio) was added to homogenates for drug extraction. Dried samples were redissolved in methanol and subjected to LCMS or MALDI-TOF analysis, respectively. Chromatography separation was performed on a Shimadzu Premier C18 column (3.0 μm, 4.6×100 mm) using a Shimadzu HPLC-MS 2020 system (Shimadzu MS Technologies, Japan). Mass spectrometry was carried out on a Shimadzu 2020 mass spectrometer with an ESI interface operating in positive ion mode. For MALDI-TOF analysis, dried samples collected from different organs (liver, kidneys, and tumor xenografts) were redissolved in methanol and subjected for analysis using a Bruker Autoflex Speed MALDI-TOF System.
Figure 10:
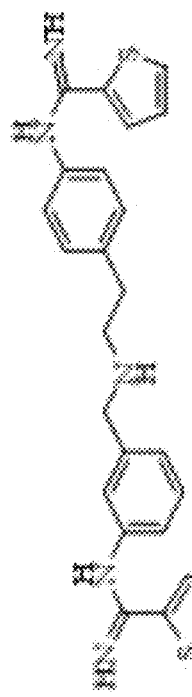
Figure 10:
Figure 10:
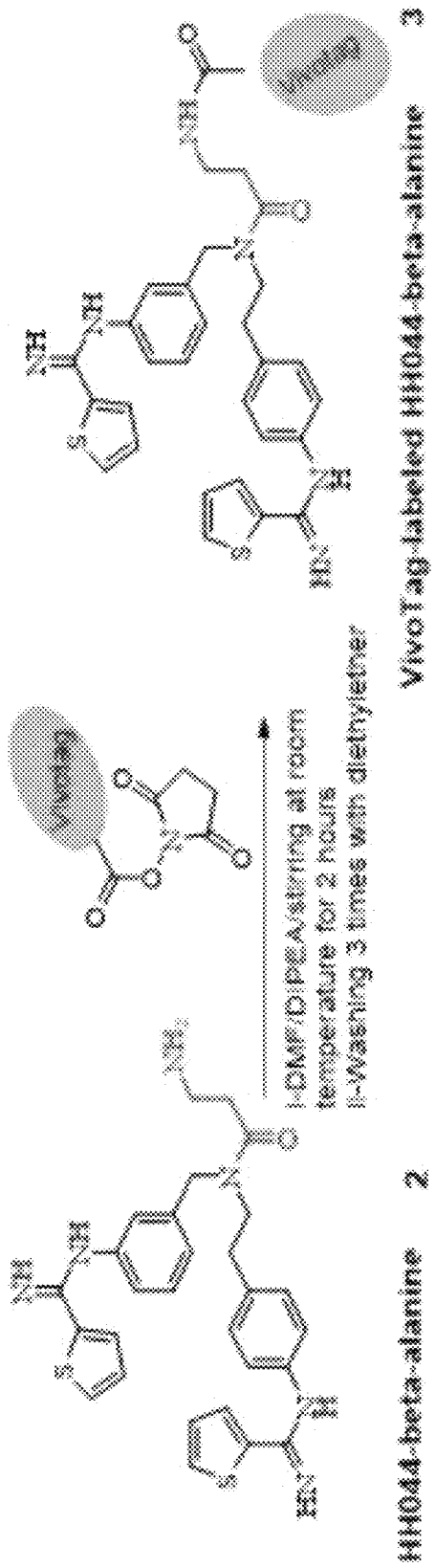
Figure 10:
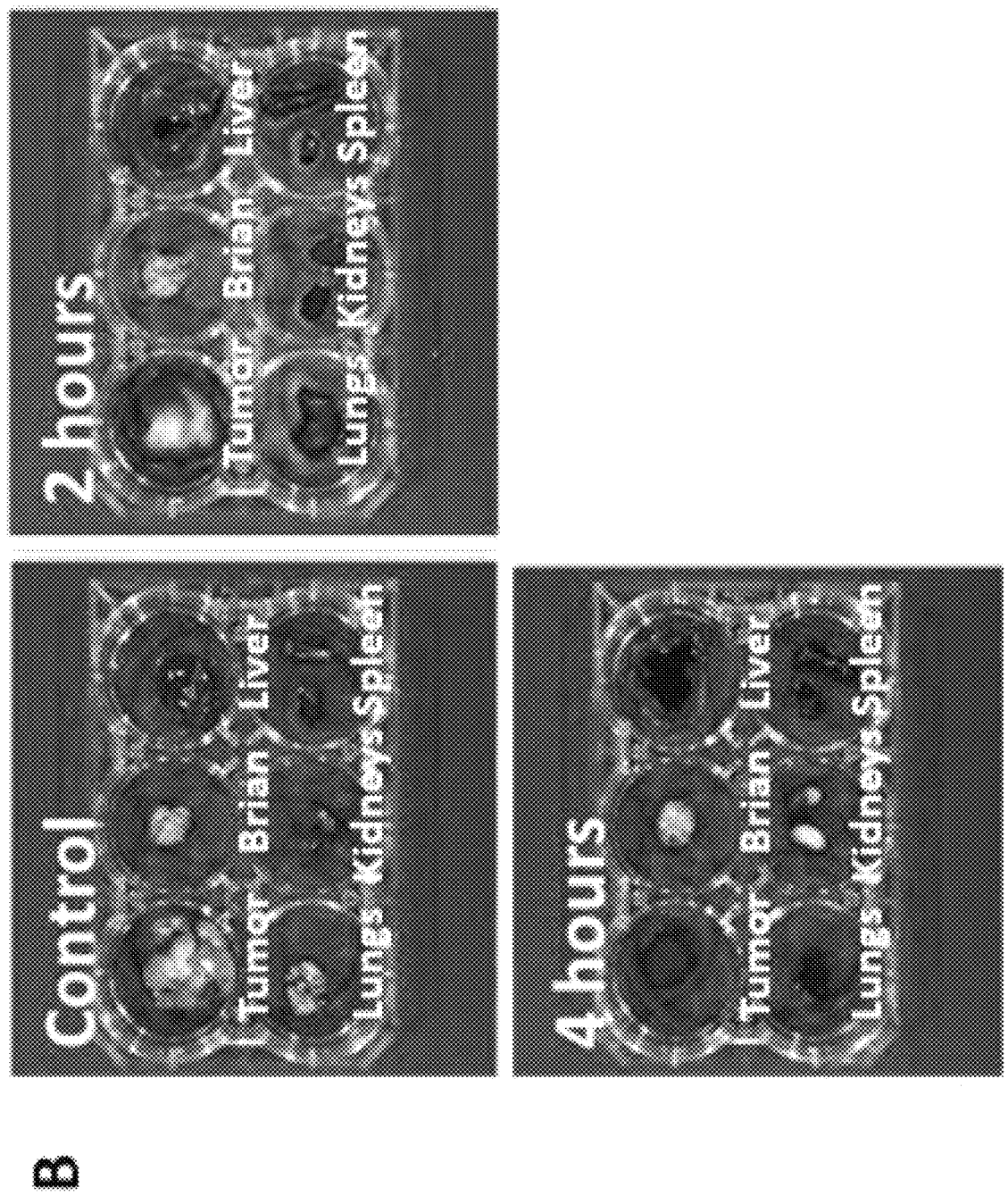
Figure 10:
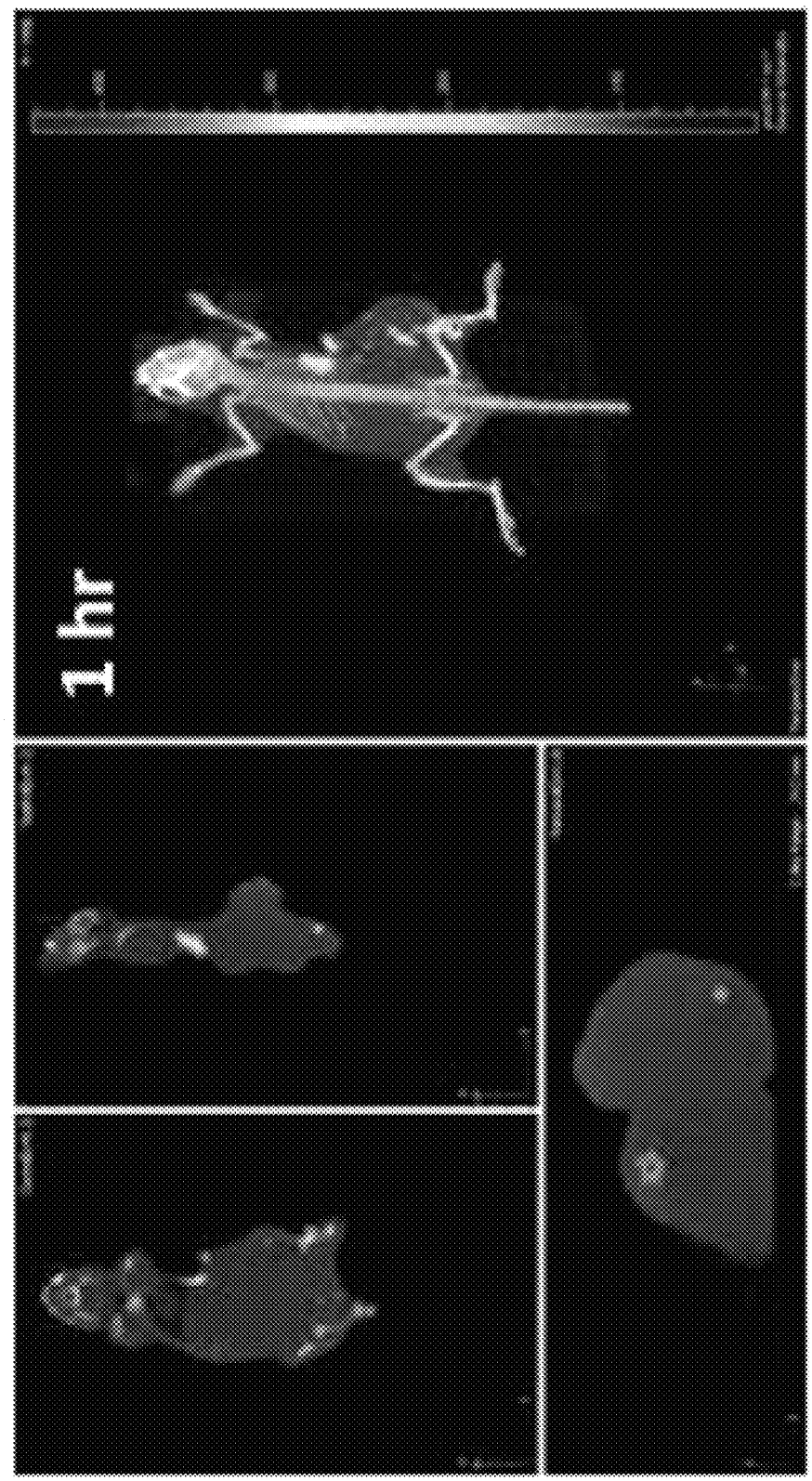
Figure 10:
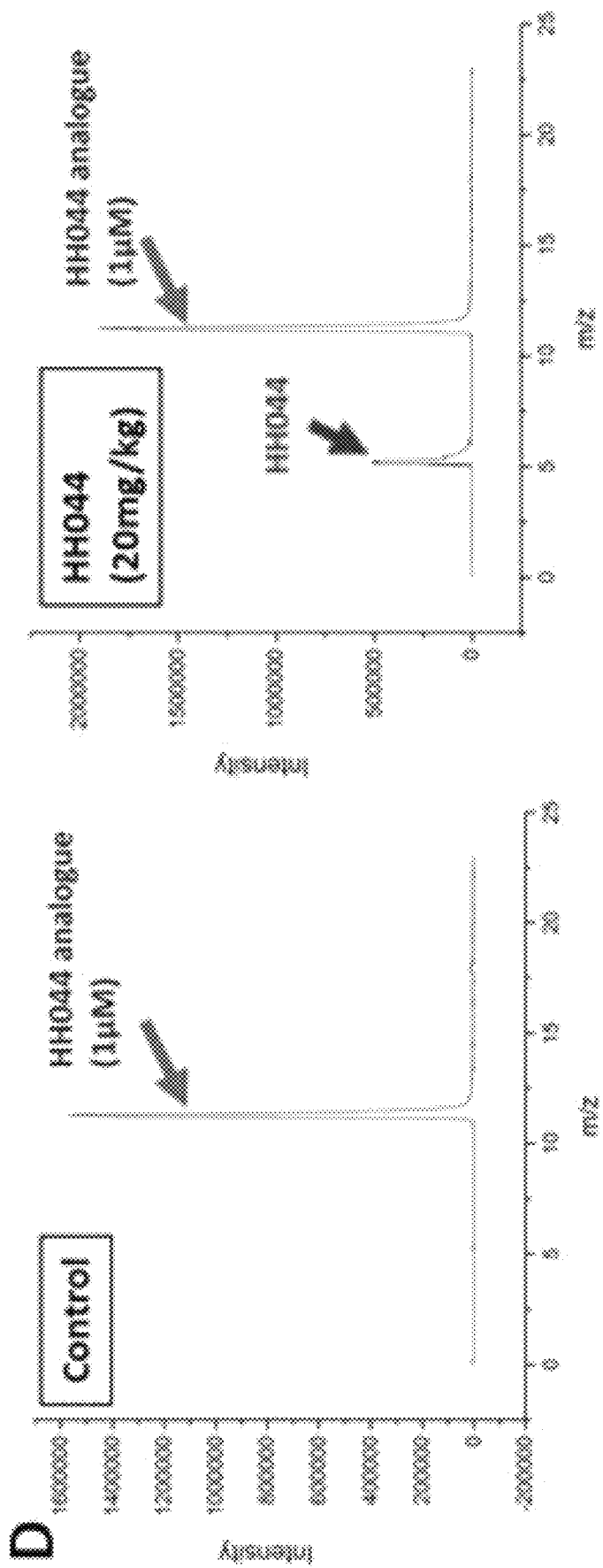
Figure 10:
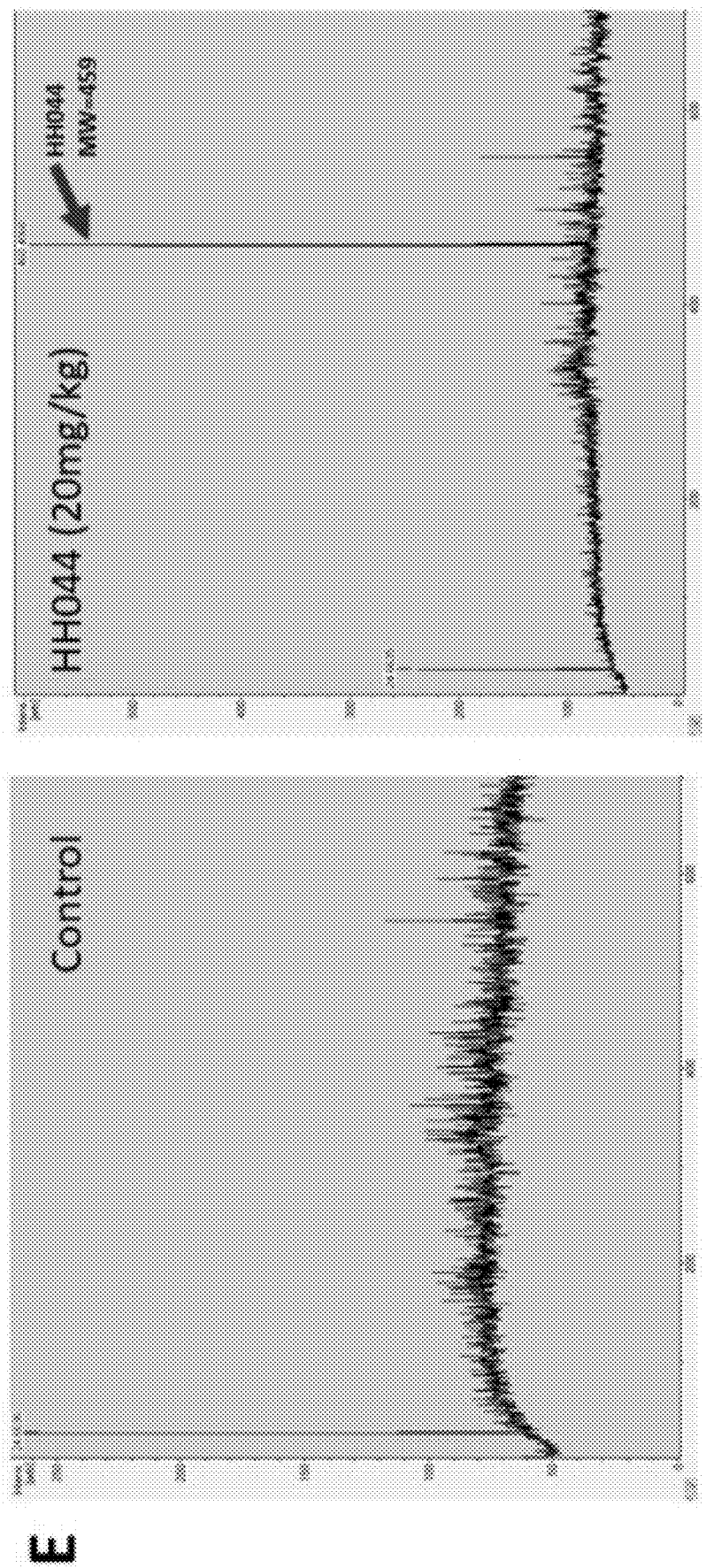

In Vivo Drug Distribution Imaging Study a) Synthesis of VivoTag 680XL-labeled HH044: As shown in our synthesis scheme (FIG. 10), first, we attached β-alanine as a linker with the primary amine to 17114044 (1). A mixture of β-alanine (1.2 mg, 0.0065 mmole, 1.2 equiv) and HATU (2.48 mg, 0.0065 mmole, 1.2 equiv) were dissolved in 200 µL of anhydrous DMF. Diisopropylethylamine (5.6 µl, 0.033 mmole, 6 equiv) was added to the solution of HH044 (1) (2.5 mg, 0.00544 mmole) after dissolving in 200 µL anhydrous DMF. The reaction mixture was stirred at room temperature for 2 h. Then 15 mL of diethyl ether was added to the reaction mixture to precipitate the product. The precipitated compound was dissolved in H$_2$O/acetonitrile and purified by HPLC using water/acetonitrile as gradient solvents. The HH044-β-alanine with the terminal NH$_2$ protected by Boc was eluted with a retention time of 47 min. The Boc protecting group was removed from the β-alanine linker using 3M HCl in methanol with stirring for 2 h. The solvent was then evaporated, and the compound was re-dissolved in 50 µL of methanol, followed by addition of 15 mL of anhydrous cold diethyl ether to precipitate compound 2. MALDI-TOF (m/z) for compound 2 (HH044-β-alanine) with a molecular formula of [C$_{28}$H$_{30}$N$_6$OS$_2$], calculated as 530.1923, gave a mass of 531.1438 [M+H].

Next, we conjugated the in vivo fluorescence tag VivoTag 680XL to HH044-β-alanine. HH044-β-alanine, with the free β-amino group (2) (71 µg, 0.135 µmole), was dissolved in 100 µL of anhydrous DMF containing 5 µL of DIPEA as a base catalyst. Then, the solution of VivoTag 680 XL (250 µg, 0. 0.135 µmole), dissolved in 100 µL of anhydrous DMF, was added to the solution of compound 2. The mixture was stirred at room temperature for 2 h. After the reaction was completed, cold diethyl ether was added to precipitate the VivoTag-labeled HH044-β-alanine (compound 3), which was washed three times with cold diethyl ether and vacuum dried for further imaging study.

b) In vivo and ex vivo imaging: 4 µg of Vivotag 680 labeled HH044 was injected to the mice via the tail vein. The animals were then scanned at different time intervals using the IVIS Spectrum imaging system (PerkinElmer, Waltham, MA). For scanning the in vivo fluorescence generated from the Vivotag 680-labeled HH044, mice were imaged at automatic timing with medium binning and F/stop 2 at an excitation and emission wavelength of 675 and 720 nm, respectively.

For ex vivo fluorescence imaging, at defined time intervals (0, 2, and 4 h) following intravenous injection, animals were euthanized; xenograft tumor, brain, liver, lungs, kidneys, spleen, and heart were excised and briefly washed with normal saline. The collected organs were then imaged using the IVIS Spectrum imaging system at automatic timing with medium binning and F/stop 2 at an excitation and emission wavelength of 675 and 720 nm, respectively.

Results

Figure 9:
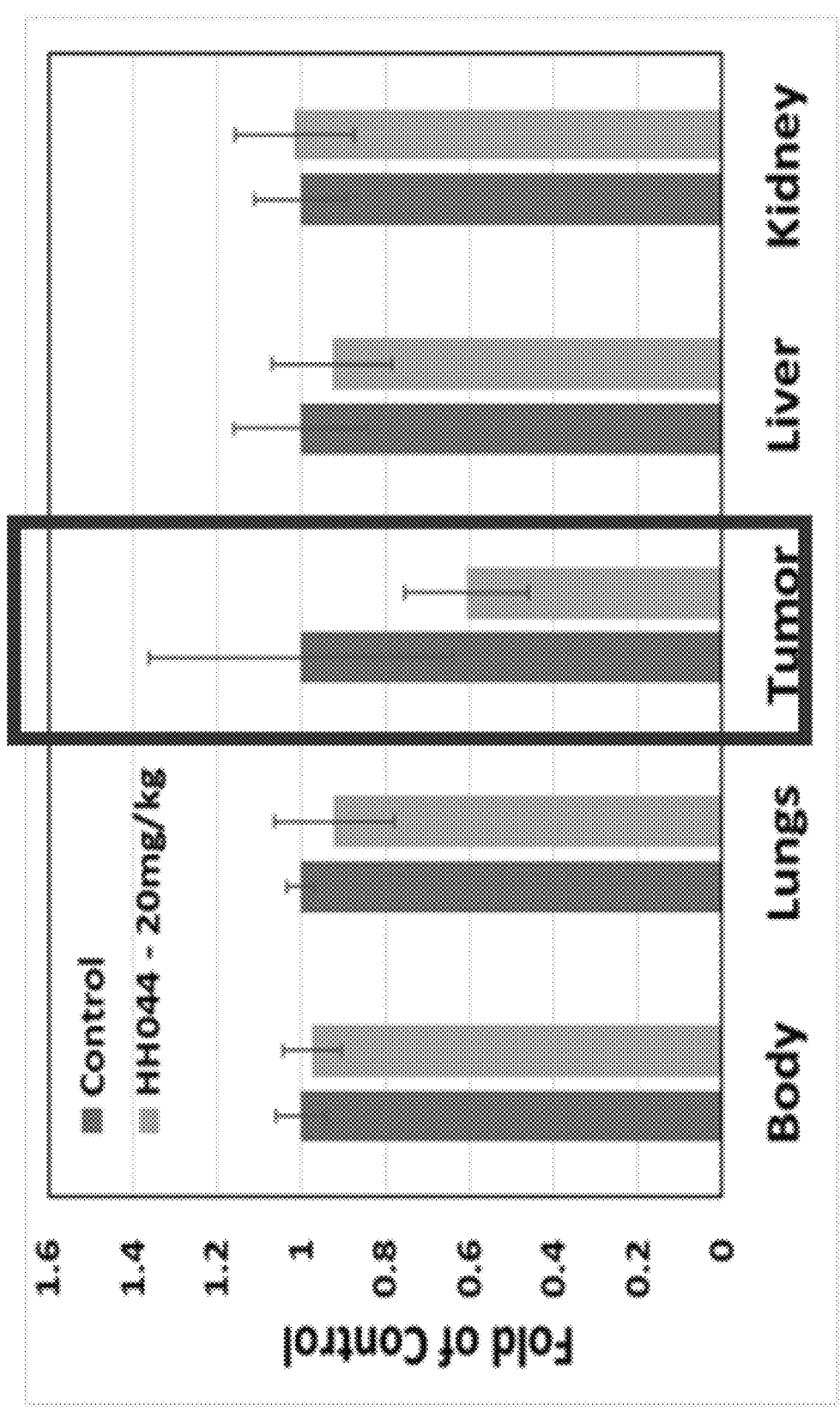
FIG. 9. Promising anti-melanoma activity of novel nNOS inhibitor HH044. Metastatic melanoma A375 cells were injected into nude mice subcutaneously on the flank. The growth of the tumor was measured daily, and tumor volume was determined with digital calipers using the formula $(length/2)\times(width)^2$. A) nNOS inhibitor HH044 (20 mg/kg) inhibited the tumor growth of human melanoma in vivo. By the end of the study the tumors (g), lungs, kidneys, livers (mg/g body weight), and body weight (g) were measured and recorded. Data are represented as mean±SD (n=5). B) and C): HH044 treatment significantly reduced in vivo PD-L1 expression. After treatment for 21 days, xenografted tumors were collected and dissociated to make single cell suspensions. The fixed cells were then stained with Alexa Fluor 488 conjugated PD-L1 antibody and the relative PD-L1 expression level was determined by flow cytometry (n=4, one tumor sample was too small to collect single cell suspension). *$p<0.05$, compared to control.
Figure 9:
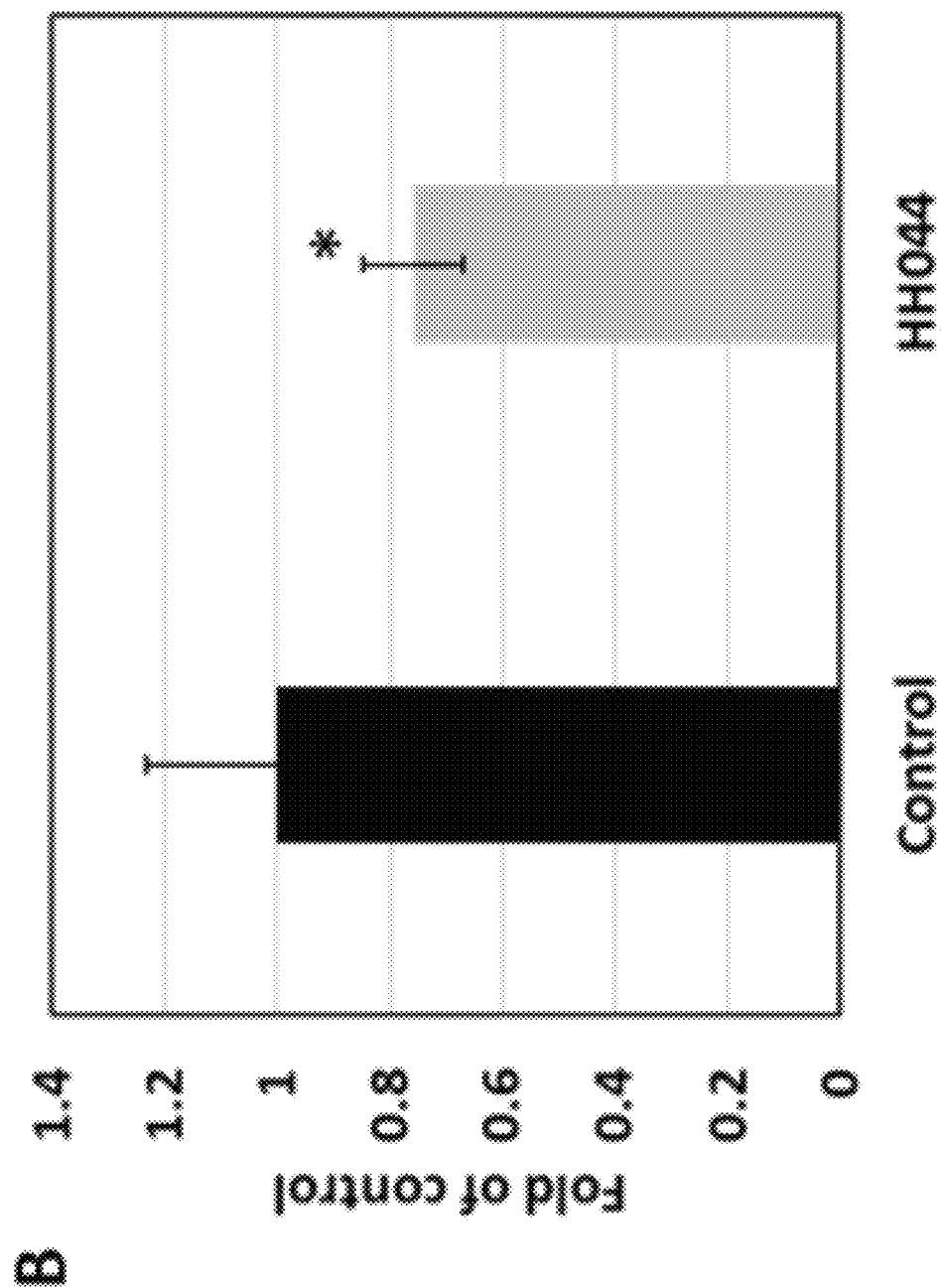
Figure 9:
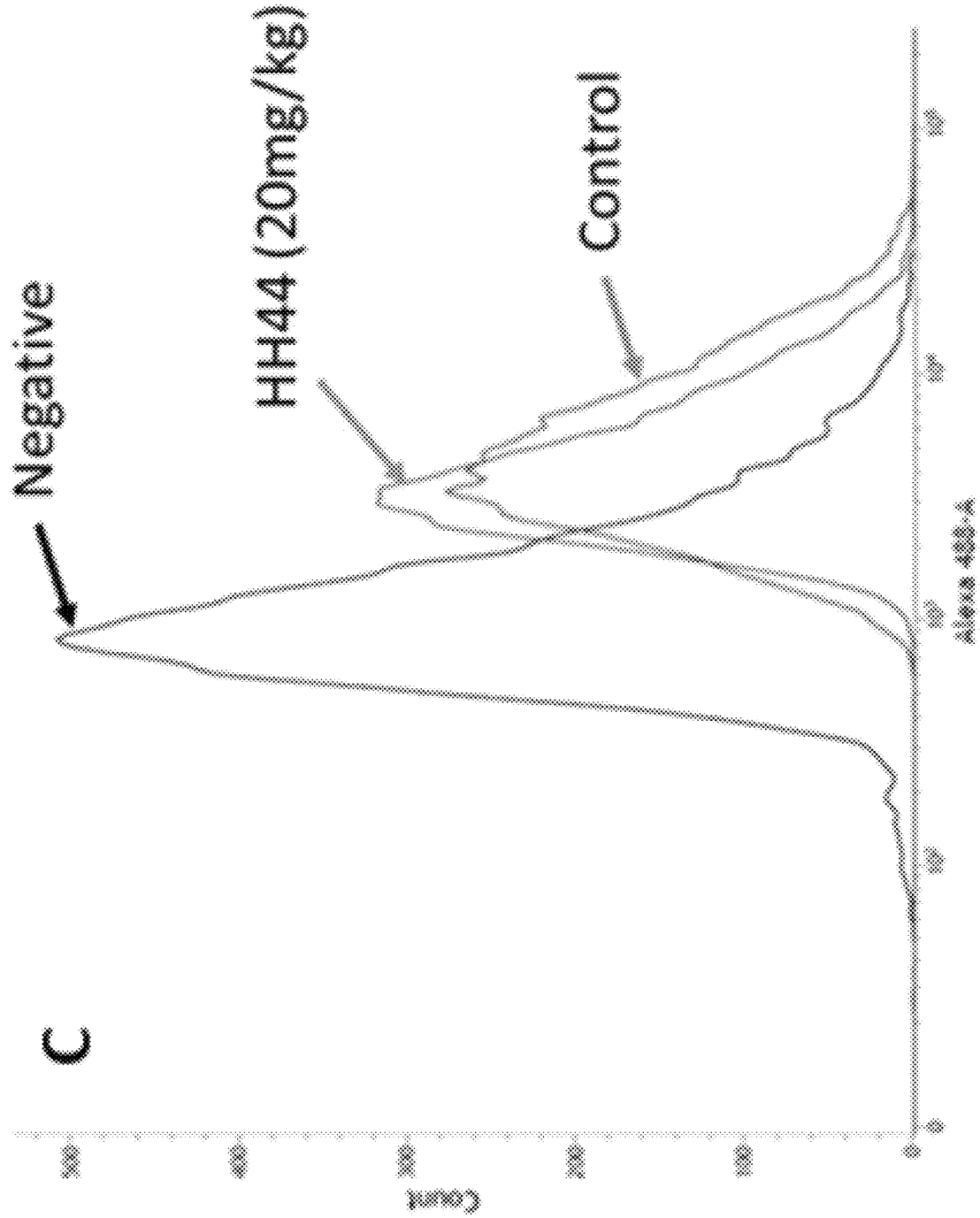

At the end of the treatment, the body, tumor, and major organs (lungs, liver, and kidneys) were weighed. In mice treated with 20 mg/kg/day of HH044 for 21 days, the final tumor weight was reduced to 61% of that of control, with no significant changes in lung, liver, and kidney weights (FIG. 9A-B). Given the small sample size of our preliminary study (n=5), the differences of tumor weight between the treatment and control groups were not statistically significant (p=0.054). There were no significant systemic toxicities observed during the entire study period. A slight decrease in body weight was observed in mice receiving the HH044 treatment (22.6 g vs. 23.9 g in control group), but this reduction is <10% and not statistically significant (p>0.05).

As shown in FIG. 9C, analysis of cell suspensions collected from A375 melanoma xenografts demonstrated a significant reduction of PD-L1 expression levels in tumors after HH044 treatment to 76% of control group (p<0.05, n=5).

To further determine the in vivo distribution of HH044, samples were collected from different organs including tumor xenografts, liver, brain, and kidneys. MALDI-TOF analysis was conducted, which confirmed the presence of HH044 observed in the tumors (FIG. 10E), liver, and kidneys (data not shown). These samples were further analyzed using LC-MS. The estimated HH044 levels calculated by the internal control (1 µM) and the area under the curve showed that HH044 reached a concentration of 0.88 µM in tumor xenografts, which was over 170-fold that of its Ki value of nNOS inhibition (0.005 µM) (FIG. 10D). These data indicate that HH044 may achieve a sufficient level in the tumors to effectively inhibit nNOS activity in vivo. LC-MS analysis also showed that the compound was found in the liver and kidney at concentrations of 3.95 and 6.00 respectively, 24 h after i.p administration, which indicates that HH044 may be metabolized and eliminated via hepatic and renal routes.

As shown in FIGS. 10B and 10C, we also studied the in vivo distribution of HH044 in live Nu/Nu mice xenografted with A375 melanoma tumors using an IVIS imaging system. Our results showed that the labeled HH044 quickly distributed to the xenografted tumor within 10 min, which remains visible up to 4 h after IV administration. Ex vivo imaging following excision of the tumor and organs confirmed a similar pattern. At 2 h post administration, the compound was mainly localized in the tumor and was also visible in the kidneys and liver but to a lesser extent. By 4 h, the compound was still observed in the tumor and livers, while predominately visible in kidneys. The consistent increased presence of drug in the liver and kidneys indicates that drug metabolism and elimination are mainly processed by these two organs. Of note, both in vivo and ex vivo imaging studies showed that no drug was observed in any of the examined brains, indicating a lack of blood brain barrier penetration.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for administering immunotherapy to a subject in need thereof, the method comprising administering to the subject an effective amount of an inhibitor of neuronal nitric oxide synthase (nNOS) for inducing an immunotherapeutic response in the subject,
   wherein the subject has a disease or disorder characterized by elevated expression levels of programmed death-ligand 1 (PD-L1), and wherein the inhibitor of nNOS is compound MAC-3-190 having a formula:

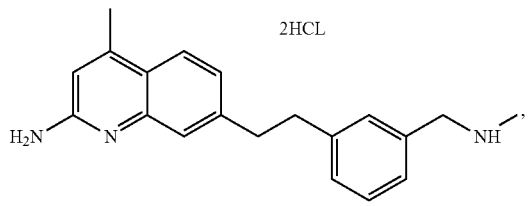 [SMILES: CNCc1cccc(CCc2ccc3c(C)cc(N)nc3c2)c1]

or suitable pharmaceutical salts, solvates, or hydrates thereof, or compound HH044 having a formula:

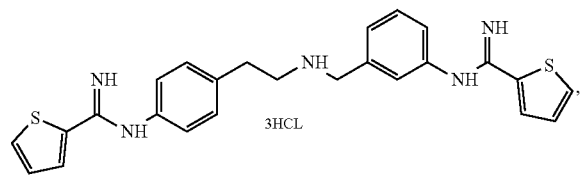 [SMILES: N=C(Nc1ccc(CCNCc2cccc(NC(=N)c3cccs3)c2)cc1)c1cccs1]

or suitable pharmaceutical salts, solvates, or hydrates thereof.

2. The method of claim 1, wherein the immunotherapeutic response includes a decrease in expression of programmed death-ligand 1 (PD-L1).

3. The method of claim 1, wherein the subject has a disease or disorder characterized by elevated expression levels of nNOS.

4. The method of claim 1, wherein the inhibitor of nNOS is the compound MAC-3-190 having the formula:

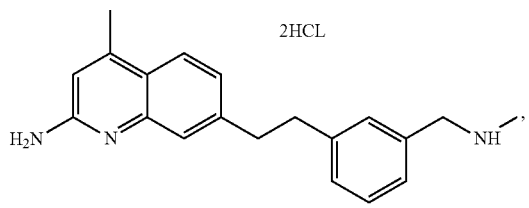 [SMILES: CNCc1cccc(CCc2ccc3c(C)cc(N)nc3c2)c1]

or suitable pharmaceutical salts, solvates, or hydrates thereof.

5. The method of claim 1, wherein the inhibitor of nNOS is the compound HH044 having the formula:

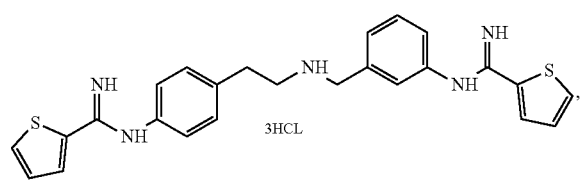 [SMILES: N=C(Nc1ccc(CCNCc2cccc(NC(=N)c3cccs3)c2)cc1)c1cccs1]

or suitable pharmaceutical salts, solvates, or hydrates thereof.

6. The method of claim 1, further comprising administering to the subject IFN-α.

7. The method of claim 1, further comprising administering to the subject a PD-L1 inhibitor or a PD-1 inhibitor.

8. The method of claim 1, further comprising administering to the subject an immune checkpoint inhibitor.

9. The method of claim 8, wherein the immune checkpoint inhibitor is selected from a programmed death-ligand 1 inhibitor, a programmed death-receptor 1 inhibitor, a cytotoxic T lymphocyte antigen 4 inhibitor, and any combination thereof.

10. The method of claim 1, further comprising administering an alkylating agent.

11. The method of claim 10, wherein the alkylating agent is selected from dacarbazine, temozolomide, and a combination thereof.

12. The method of claim 1, wherein the inhibitor of nNOS is administered orally.

13. A method for treating a melanoma characterized by elevated expression levels of programmed death-ligand 1 (PD-L1) in a subject in need thereof, the method comprising administering to the subject an inhibitor of neuronal nitric oxide synthase (nNOS) for decreasing expression of PD-L1 and one or more additional therapeutic agents, wherein the inhibitor of nNOS is the compound MAC-3-109 having a formula:

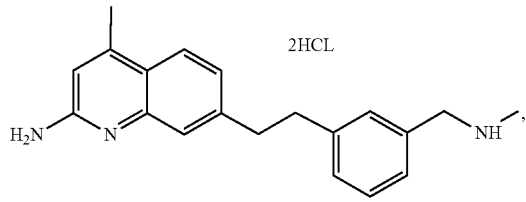 [SMILES: CNCc1cccc(CCc2ccc3c(C)cc(N)nc3c2)c1]

or suitable pharmaceutical salts, solvates, or hydrates thereof, or the inhibitor of nNOS is the compound HH044 having a formula:

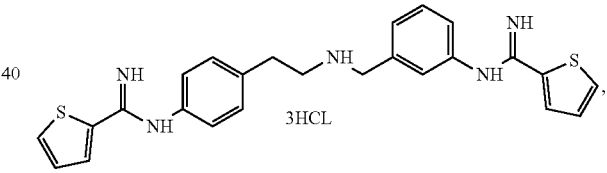

or suitable pharmaceutical salts, solvates, or hydrates thereof.

14. The method of claim 13, wherein the one or more additional therapeutic agents comprise an immune checkpoint inhibitor.

15. The method of claim 14, wherein the one or more additional therapeutic agents comprise an immune checkpoint inhibitor selected from a programmed death-ligand 1 inhibitor, a programmed death-receptor 1 inhibitor, a cytotoxic T lymphocyte antigen 4 inhibitor, and any combination thereof.

16. The method of claim 15, wherein the one or more additional therapeutic agents comprise a programmed death-ligand 1 inhibitor or a programmed death-receptor 1 inhibitor.

17. The method of claim 16, wherein the PD-L1 inhibitor is selected from Atezolizumab, Avelumab, Durvalumab, BMS-936559, and CK-301.

18. The method of claim 16, wherein the PD-1 inhibitor is selected from Pembrolizumab and Nivolumab.

19. The method of claim 13, wherein the one or more additional therapeutic agents comprise IFN-α.

20. The method of claim 13, wherein the one or more additional therapeutic agents comprise an alkylating agent.

21. The method of claim 20, wherein the one or more additional therapeutic agents comprise an alkylating agent selected from dacarbazine, temozolomide, and a combination thereof.

22. The method of claim 13, wherein the inhibitor of nNOS is administered orally.

23. The method of claim 13, wherein the inhibitor of nNOS is the compound MAC-3-190 having the formula:

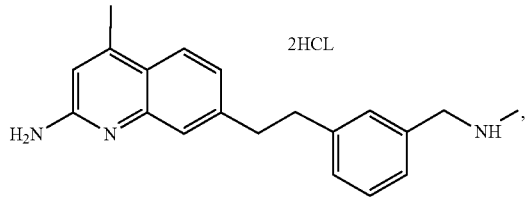 [SMILES: CNCc1cccc(CCc2ccc3c(C)cc(N)nc3c2)c1]

or suitable pharmaceutical salts, solvates, or hydrates thereof.

24. The method of claim 13, wherein the inhibitor of nNOS is the compound HH044 having the formula:

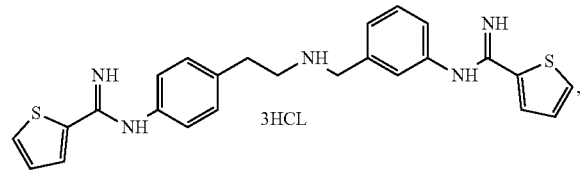 [SMILES: N=C(Nc1ccc(CCNCc2cccc(NC(=N)c3cccs3)c2)cc1)c1cccs1]

or suitable pharmaceutical salts, solvates, or hydrates thereof.

* * * * *